United States Patent
Nguyen-Kim et al.

(10) Patent No.: US 9,951,165 B2
(45) Date of Patent: Apr. 24, 2018

(54) CATIONIZABLE RHEOLOGY MODIFYING AND SETTING MEANS, COMPOSITION THEREOF AND METHOD OF MAKING BOTH

(71) Applicant: BASF SE, Ludwigshafen (DE)

(72) Inventors: Son Nguyen-Kim, Hemsbach (DE); David Graham, Düsseldorf Altstadt (DE); Holger Türk, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/648,462

(22) PCT Filed: Nov. 20, 2013

(86) PCT No.: PCT/EP2013/074245
§ 371 (c)(1),
(2) Date: May 29, 2015

(87) PCT Pub. No.: WO2014/082904
PCT Pub. Date: Jun. 5, 2014

(65) Prior Publication Data
US 2015/0315323 A1     Nov. 5, 2015

Related U.S. Application Data

(60) Provisional application No. 61/731,585, filed on Nov. 30, 2012.

(30) Foreign Application Priority Data

Nov. 30, 2012    (EP) .................................... 12195180

(51) Int. Cl.
| | | |
|---|---|---|
| A61Q 5/12 | (2006.01) | |
| C08F 226/10 | (2006.01) | |
| C08L 39/06 | (2006.01) | |
| A61K 8/81 | (2006.01) | |
| A61Q 5/06 | (2006.01) | |
| C08F 220/18 | (2006.01) | |
| C08L 33/14 | (2006.01) | |
| A61Q 19/00 | (2006.01) | |
| C08F 220/14 | (2006.01) | |

(52) U.S. Cl.
CPC ............ *C08F 226/10* (2013.01); *A61K 8/817* (2013.01); *A61K 8/8152* (2013.01); *A61K 8/8182* (2013.01); *A61Q 5/06* (2013.01); *A61Q 5/12* (2013.01); *A61Q 19/00* (2013.01); *C08F 220/18* (2013.01); *C08L 33/14* (2013.01); *C08L 39/06* (2013.01); *A61K 2800/22* (2013.01); *A61K 2800/48* (2013.01); *A61K 2800/54* (2013.01); *C08F 220/14* (2013.01); *C08F 2220/1825* (2013.01)

(58) Field of Classification Search
None
See application file for complete search history.

(56) References Cited

U.S. PATENT DOCUMENTS

| 8,398,963 B2 | 3/2013 | Kim et al. |
| 2008/0089853 A1 | 4/2008 | Nguyen-Kim et al. |
| 2010/0068156 A1 | 3/2010 | Kim |

FOREIGN PATENT DOCUMENTS

WO     WO-01/62809     8/2001

OTHER PUBLICATIONS

PCT International Search Report in PCT/EP2013/074245, dated Dec. 12, 2013, 4 pages.
Directive 2004/42/CE of the European Parliament and of the Council of Apr. 21, 2004, *Official Journal of the European Union* Apr. 30, 2004, 10 pages.
PCT International Preliminary Report on Patentability in PCT/EP2013/074245, dated Jun. 2, 2015, 4 pages.
PCT International Written Opinion in PCT/EP2013/074245, dated Jun. 5, 2014, 3 pages.

*Primary Examiner* — Jyothsna A Venkat
(74) *Attorney, Agent, or Firm* — Marshall, Gerstein & Borun LLP

(57) ABSTRACT

Provided are: a copolymer for rheological or cosmetic compositions and, a composition thereof, and methods of making and using the same. Said copolymer comprises
a) a first acrylic ester as monomer A, said monomer A being a branched acrylic ester;
b) at least one further acrylic ester as monomer B, said monomer B being a linear acrylic ester;
c) a cyclic N-vinyl amide as monomer C;
d) at least one compound comprising a radically polymerizable $\alpha.\beta$-ethylenically un-saturated double bond and at least one cationic and/or cationogenic moiety said compound being monomer D;
e) at least one monoethylenically unsaturated carboxylic acid as monomer E; with the monomer B in its polymerized form having a glass transition temperature of 24° C. or lower and making at most one third of the weight amount of monomer A.

5 Claims, 6 Drawing Sheets

CATIONIZABLE RHEOLOGY MODIFYING AND SETTING MEANS, COMPOSITION THEREOF AND METHOD OF MAKING BOTH

CROSS-REFERENCE TO RELATED APPLICATIONS

This application is the National Stage entry of PCT/EP2013/074245, filed on Nov. 20, 2013, which claims priority to European Application Number 12195180.0, filed on Nov. 30, 2012, and U.S. Ser. No. 61/731,585 filed on Nov. 30, 2012, which are incorporated herein by reference in their entireties.

TECHNICAL FIELD

The present invention deals with a copolymer for rheological or cosmetic compositions, a process of making it, a composition thereof and a method of producing said composition. Also within the scope of the invention are selected uses of either the copolymer or the composition thereof which are equivalent to selected methods of using of either the copolymer or the composition of the invention.

BACKGROUND

The technology of providing copolymers and cosmetic compositions satisfying several demands of modern rheology modifiers or cosmetic polymers is already highly advanced.

WO 01/62809 A1 describes a cosmetic means comprising at least one water-soluble or water-dispersible polymer which comprises in incorporated form a) 5 to 50% by weight of at least one α,β-ethylenically unsaturated monomer of formula I

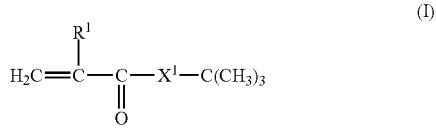

in which $R^1$ is hydrogen or $C_1$-$C_8$-alkyl, and $X^1$ is O or $NR^2$, where $R^2$ is hydrogen, $C_1$-$C_8$-alkyl or $C_5$-$C_8$-cycloalkyl, b) 25 to 90% by weight of at least one N-vinylamide and/or N-vinyllactam, c) 0.5 to 30% by weight of at least one compound having a free-radically polymerizable, α,β-ethylenically unsaturated double bond and at least one cationogenic and/or cationic group per molecule, d) 0 to 30% by weight of at least one α,β-ethylenically unsaturated monomer of formula II

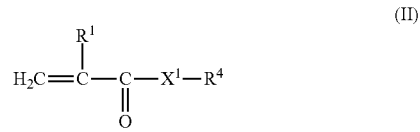

in which $R^3$ is hydrogen or $C_1$-$C_8$-alkyl, $X^2$ is O or $NR^5$, where $R^5$ is hydrogen, $C_1$-$C_8$-alkyl or $C_5$-$C_8$-cycloalkyl, and $R_4$ is hydrogen or a linear $C_1$-$C_{22}$-alkyl radical or the salts thereof.

One polymer of this disclosure comprises 30% by weight of tert.-butylacrylate, 19% by weight of n-butylacrylate, 27% by weight of N-vinylpyrrolidone, 17% by weight of N-(3-(dimethylamino)propyl)acrylamide in an about 90% protonated form, 5% by weight of methacrylic acid and 2% by weight of an ethoxylatet polysiloxane (Belsil® DMC 6031, Wacker).

However said polymer is still to be optimized with respect to its performance and price characteristics. First of all, using an additional ethoxylated polysiloxane makes production costs higher. Furthermore said monomer confers a certain softness to the polymer which would lead to somewhat less stable since higher flexible polymer films. This same effect is known to be generated from acrylic esters like n-butylacrylate, since this monomer likewise has a soft character. However, weak and highly flexible polymer films on ceratinic surfaces or the skin would render a hair style or a cream layer more unstable during time, especially in windy or rainy weather and at the worst would completely disintegrate the hair style formed or the cream layer applied. This effect can be partially attenuated by means of applying a larger amount of polymer respectively cosmetic means or by repeatedly applying it, thus resulting in higher costs per application or per effect desired.

Completely omitting n-butylacrylate or both n-butylacrylate and the ethoxylated polysiloxane from the water-soluble or water-dispersible polymer of the cosmetic means as indicated for certain of the WO 01/62809 A1 embodiments comprising the combination of a), b) c) and d) supra would not improve the situation either, since then a rigid polymer film will form on the hair or skin. Said rigid film is able to properly maintain the shape of a hairstyle, if said hair style remains mechanically unaffected or almost unaffected. However, repeated hair combing, brushing, moving through it with the hands or even windy weather will bent the somewhat rigid polymer film and partially lead it to break. A consequence thereof is that conditioning and styling performance will drop and polymer flakes will trickle out of the hair do or from other ceratinic surfaces or the skin, a perturbing and unpleasant situation especially for dark-haired people. This effect can unfortunately not be neglected since such polymer in solution per se is already turbid not transparent, whereas transparency would reduce perception of polymer-born flakes. A further drawback of such even reduced polymer flaking is that one inescapably would require more of polymer per application or more applications per time in order to come to a sufficient and long lasting conditioning, styling or setting effect. This again would make the cosmetic means more expensive.

These are only some of the drawbacks of the prior art which are to overcome.

SUMMARY

One object of the invention is to provide a copolymer having both good setting and conditioning properties and being highly compatible with propellants. The copolymer shall be readily soluble in solvents and even highly water-loaded solvents and at the same time shall homogeneously adhere to a ceratinic surface or to the skin once the solvent being removed. Said adherence shall not be effected by low amounts of water i.e. rain drops and preferably shall only be disrupted by detergent-containing e.g. body wash products. It is another requirement for the copolymer of the invention to act as mediator between thickeners and styling polymers, which otherwise cannot be homogeneously mixed. Said inventive copolymer shall be cost-effective which means either the copolymer per se can be cheaply obtained or it is used in lower amounts compared to copolymers of the prior art without suffering a loss of styling- and/or conditioning performance on ceratinic surfaces or the skin to be treated. However, the copolymer of the invention, even when used in lower amounts compared to the prior art, shall confer to the ceratinic surface a smooth and glossy non-sticky feel and a fine appearance not disturbed by clumpy or clumsy copolymer aggregates or copolymer-born flakes.

Furthermore a cosmetic composition comprising at least a cosmetically acceptable carrier and the copolymer of the invention should simultaneously work as conditioner and styling or setting means. Said composition shall have a clear almost transparent aspect, even though when supplemented with a propellant as cosmetically acceptable carrier, with which a high compatibility is required. Said composition shall form a homogenous phase with the solvents used and even with highly water-loaded solvents. It is further demanded thereof to form a homogeneous spray pattern viz. a pattern only showing small sized droplets. The composition furthermore shall be readily compatible with ceratinic surfaces like for instance hair, nails and with the skin viz. adheres to them such that it can only be removed by a substantial amount of water or more preferably by detergent-supplemented aqueous solutions. Any flaking of the composition on the ceratinic surface or sticky feel should be avoided. A further object of the invention is to provide a cost-efficient cosmetic composition for instance by reducing the amount of additional copolymers (e.g. styling-thickening and/or conditioning copolymers) without hampering the overall composition performance and in particular the performance of the copolymers thereof.

Both inventive copolymer and inventive cosmetic composition are further required to be non-hazardous, even when applied in a finely dispersed spray.

Highly compatible with propellants means, that a container filled with the copolymer or the composition of the invention, when supplemented with a propellant, shall not lead to a turbid aspect of said copolymer-propellant mixture or of the said composition. Highly compatible also means that the copolymer-propellant mixture or the composition does not clog a spraying means like e.g. a nozzle by which the copolymer-propellant mixture or the composition is finely dispersed onto a surface like e.g. a hair do, the skin or a nail surface. The hair and/or the nails are understood within this application to form the ceratinic surface.

It was shown in a large number of experiments that the copolymers or polymers (where the term polymer and copolymer are alternately used in this text) disclosed in claim 1 are able to meet the requirements as set forth previously.

DETAILED DESCRIPTION

The terms "copolymer" or "copolymer of the invention" as well as "polymer" and "polymer of the invention" and their respective plural forms in this text are interchangeable if not expressly indicated otherwise.

If the term "meth" within methacrylate or methacrylamide is written within parentheses like (meth)acrylate or (meth)acrylamide, this means that both acrylate and methacrylate or acrylamide and methacrylamide as compound type are disclosed.

An inventive composition also referred to as a cosmetic composition or a cosmetic composition of the invention at least comprises water and/or an organic solvent and/or a VOC (VOC means volatile organic compound) and the copolymer of the invention. The same applies for a rheological composition or a rheological composition of the invention which likewise is an inventive composition.

Main features of the invention are shown in claims 1, 13, 14 and 15 whereas further inventive embodiments can be gathered from claims 2 to 12 and the subsequent detailed explanation of the claims.

The invention discloses a copolymer for rheological or cosmetic compositions comprising a first acrylic ester as monomer A, said monomer A being a branched acrylic ester; at least one further acrylic ester as monomer B, said monomer B being a linear acrylic ester; a cyclic N-vinyl amide as monomer C; at least one compound comprising a radically polymerizable $\alpha.\beta$-ethylenically unsaturated double bond and at least one cationic and/or cationogenic moiety said compound being monomer D and at least one monoethylenically unsaturated carboxylic acid as monomer E. It is important for the invention to use as monomer B only such compound which when polymerized provides a glass transition temperature of 24° C. or lower and said monomer B being employed in a quantity making at most one third of the weight amount of monomer A.

Provided one chooses monomers B with a glass transition temperature above 24° C. the copolymers thus formed are more brittle and films obtained from cosmetic compositions thereof tend at least partially to break thus provoking flaking to occur and increasing the amount of copolymer to be required for a certain rheological or cosmetic effect. However, if on the other hand the weight amount of monomer B exceeds one third of the weight amount of monomer A, the flexibility of the monomeric side chains of the copolymer increases such that a cosmetic composition thereof will form quite soft copolymer films on a hair do or a ceratinic surface. Consequently styling performance of such copolymer tends to drop. Furthermore, this also impacts on the particle size of a cosmetic composition and thus on the required uniform distribution of copolymers of said composition applied to a ceratinic surface or onto the skin.

All these drawbacks are to be avoided by means of the inventive copolymers. Since maximum styling performance can be obtained with such copolymers, their amount to be required in a cosmetic composition of the invention is reduced thus also reducing the production costs and consumption costs of such composition. Furthermore the demands as given supra are completely met by the inventive copolymer as will be further detailed below.

The monomer A, viz. the branched acrylic ester of the invention comprises an ester moiety stemming from secondary or tertiary alcohols, preferably from tertiary alcohols. It preferably is selected from the group consisting of isopropyl acrylate, 2-ethyl butyl acrylate, 2-ethyl hexyl acrylate, sec-butyl acrylate, isobutyl acrylate, tert-butyl acrylate, 2-pentyl acrylate, 2-methyl butyl acrylate, 3-methyl butyl acrylate, 3-pentyl acrylate, isopentyl acrylate, neopentyl acrylate, 2-methyl pentyl acrylate, 2-heptyl acrylate, 2-octyl acrylate, 2-methyl-7-ethyl-4-undecyl acrylate and mixtures thereof. Tert.-butyl acrylate or mixtures which comprise tert.-butyl acrylate are particularly preferred. In a mostly preferred embodiment monomer A is tert-butylacrylate since the bulky tert.-butyl moiety thereof is a perfect counterpart to monomer B.

Said monomer B is at least one further acrylic ester selected from the group consisting of linear acrylic esters. Linear within the scope of this disclosure means that monomers B are used which are obtained upon reacting acrylic acid or an acrylic halide with an n-alkyl alcohol viz. an alcohol comprising one hydroxyl group and an n-alkyl moiety. N-alkyl comprises the entities methyl, ethyl, n-propyl, n-butyl, n-pentyl, n-hexyl, n-heptyl, n-octyl or capryl, n-nonyl, n-decyl, n-undecyl, n-dodecyl or lauryl, n-tridecyl, n-tetradecyl or myristyl, n-pentadecyl and higher n-alkyl homologues as long as the corresponding acrylic esters formed from the respective alcohol and acrylic acid or acrylic halide give homopolymers having a glass transition temperature of 24° C. or lower.

In a further embodiment of the invention a copolymer for rheological or cosmetic compositions comprises a) a first acrylic ester as monomer A, said monomer A being a branched acrylic ester; b) at least one further acrylic ester as monomer B, said monomer B being a linear acrylic ester; c) a cyclic N-vinyl amide as monomer C; d) at least one compound comprising a radically polymerizable α.β-ethylenically unsaturated double bond and at least one cationic and/or cationogenic moiety said compound being monomer D; e) at least one monoethylenically unsaturated carboxylic acid as monomer E; with the monomer B in its polymerized form having a glass transition temperature of 10° C. or lower and making at most one third of the weight amount of monomer A.

A still more advanced embodiment of the invention seeks protection for a copolymer for rheological or cosmetic compositions comprising a) a first acrylic ester as monomer A, said monomer A being a branched acrylic ester; b) at least one further acrylic ester as monomer B, said monomer B being a linear acrylic ester; c) a cyclic N-vinyl amide as monomer C; d) at least one compound comprising a radically polymerizable α.β-ethylenically unsaturated double bond and at least one cationic and/or cationogenic moiety said compound being monomer D; e) at least one monoethylenically unsaturated carboxylic acid as monomer E; with the monomer B in its polymerized form having a glass transition temperature of 0° C. or lower and making at most one third of the weight amount of monomer A.

In a highly preferred embodiment a copolymer for rheological or cosmetic compositions comprising a) a first acrylic ester as monomer A, said monomer A being a branched acrylic ester; b) at least one further acrylic ester as monomer B, said monomer B being a linear acrylic ester; c) a cyclic N-vinyl amide as monomer C; d) at least one compound comprising a radically polymerizable α.β-ethylenically unsaturated double bond and at least one cationic and/or cationogenic moiety said compound being monomer D; e) at least one monoethylenically unsaturated carboxylic acid as monomer E; with the monomer B in its polymerized form having a glass transition temperature of −3° C. or lower and making at most one third of the weight amount of monomer A.

Likewise highly preferred is an embodiment providing a copolymer for rheological or cosmetic compositions comprising a) a first acrylic ester as monomer A, said monomer A being a branched acrylic ester; b) at least one further acrylic ester as monomer B, said monomer B being a linear acrylic ester; c) a cyclic N-vinyl amide as monomer C; d) at least one compound comprising a radically polymerizable α.β-ethylenically unsaturated double bond and at least one cationic and/or cationogenic moiety said compound being monomer D; e) at least one monoethylenically unsaturated carboxylic acid as monomer E; with the monomer B in its polymerized form having a glass transition temperature of −18° C. or lower and making at most one third of the weight amount of monomer A.

Within the same range of preference protection is sought for a copolymer for rheological or cosmetic compositions comprising a) a first acrylic ester as monomer A, said monomer A being a branched acrylic ester; b) at least one further acrylic ester as monomer B, said monomer B being a linear acrylic ester; c) a cyclic N-vinyl amide as monomer C; d) at least one compound comprising a radically polymerizable α.β-ethylenically unsaturated double bond and at least one cationic and/or cationogenic moiety said compound being monomer D; e) at least one monoethylenically unsaturated carboxylic acid as monomer E; with the monomer B in its polymerized form having a glass transition temperature of −50° C. or lower and making at most one third of the weight amount of monomer A.

One notes that great care is to be applied for selecting appropriate monomers B. This is since the glass transition temperature of their respective homopolymers (viz. of their polymerized form) decreases with the number of carbon atoms in the n-alkyl moiety of the linear alkyl chain of the monomer B, and from a certain length of said n-alkyl moiety viz. a certain number of carbons therein said glass transition temperature increases again. It is mandatory for the invention just to be within a window of glass transition temperatures in order to properly adjust the microstructure of the inventive copolymer and thus to optimize the mechanical and stability performance of a composition comprising said copolymer.

Consequently monomer B has an ester moiety selected from the group consisting of COO—$C_1$-$C_{14}$-alkyl, preferably consisting of COO—$C_2$-$C_{14}$-alkyl, more preferably consisting of COO—$C_2$-$C_{12}$-alkyl and particularly preferred consisting of COO—$C_4$-$C_{12}$-alkyl. Just for the purpose of clarity COO—$C_1$-alkyl means —COO—$CH_3$ and COO—$C_2$-$C_{12}$-alkyl comprises the entities —COO—($CH_2$)—$CH_3$, —COO—($CH_2$)$_2$—$CH_3$, —COO—($CH_2$)$_3$—$CH_3$, and so on till —COO—($CH_2$)$_{11}$—$CH_3$.

A really surprising effect with the use of monomer B is its behavior within the copolymer of the invention. More a glass transition temperature of monomer B in polymerized form is low more this monomer B should give a quite soft copolymer as mentioned supra. This is indeed what is observed if one adds a substantial amount of monomer B to the monomer mixture for polymerization. However, provided that monomer B as described supra makes at most one third of the weight amount of monomer A within the copolymer of the invention the inventive copolymer does not turn to a soft but rather to a more rigid while flexible character as can be seen from the increasing values for the flexural strength in table 2. This is astonishing but servers the requirements for copolymers or rheological or cosmetic compositions to exhibit a better styling, conditioning or rheology improving performance.

A rheological composition within the scope of this invention is any composition wherein an inventive copolymer serves for modifying the mechanical properties of said composition, for instance its viscosity, its fluidity or its tendency to refrain from disintegration.

A cosmetic composition as understood by this invention is any composition applied to the human or animal body in order to change, improve or clean ceratinic surfaces or the skin thereof. Such cosmetic composition will be further detailed infra.

In a further embodiment of the invention a copolymer for rheological or cosmetic compositions comprises a) a first acrylic ester as monomer A, said monomer A being a branched acrylic ester; b) at least one further acrylic ester as monomer B, said monomer B being a linear acrylic ester; c) a cyclic N-vinyl amide as monomer C; d) at least one compound comprising a radically polymerizable α.β-ethylenically unsaturated double bond and at least one cationic and/or cationogenic moiety said compound being monomer D; e) at least one monoethylenically unsaturated carboxylic acid as monomer E; with the monomer B in its polymerized form having a glass transition temperature of 24° C. or lower and making at most 2/7 of the weight amount of monomer A.

In yet another embodiment of the invention a copolymer for rheological or cosmetic compositions comprises a) a first acrylic ester as monomer A, said monomer A being a branched acrylic ester; b) at least one further acrylic ester as monomer B, said monomer B being a linear acrylic ester; c) a cyclic N-vinyl amide as monomer C; d) at least one compound comprising a radically polymerizable α.β-ethylenically unsaturated double bond and at least one cationic and/or cationogenic moiety said compound being monomer D; e) at least one monoethylenically unsaturated carboxylic acid as monomer E; with the monomer B in its polymerized form having a glass transition temperature of 24° C. or lower and making at most 1/7 of the weight amount of monomer A.

Still another embodiment of the invention provides a copolymer for rheological or cosmetic compositions comprises a) a first acrylic ester as monomer A, said monomer A being a branched acrylic ester; b) at least one further acrylic ester as monomer B, said monomer B being a linear acrylic ester; c) a cyclic N-vinyl amide as monomer C; d) at least one compound comprising a radically polymerizable α.β-ethylenically unsaturated double bond and at least one cationic and/or cationogenic moiety said compound being monomer D; e) at least one monoethylenically unsaturated carboxylic acid as monomer E; with the monomer B in its polymerized form having a glass transition temperature of 0° C. or lower and making at most 2/7 of the weight amount of monomer A.

A still further amended embodiment of the invention describes In a further embodiment of the invention a copolymer for rheological or cosmetic compositions comprises a) a first acrylic ester as monomer A, said monomer A being a branched acrylic ester; b) at least one further acrylic ester as monomer B, said monomer B being a linear acrylic ester; c) a cyclic N-vinyl amide as monomer C; d) at least one compound comprising a radically polymerizable α.β-ethylenically unsaturated double bond and at least one cationic and/or cationogenic moiety said compound being monomer D; e) at least one monoethylenically unsaturated carboxylic acid as monomer E; with the monomer B in its polymerized form having a glass transition temperature of 0° C. or lower and making at most 1/7 of the weight amount of monomer A.

Still another embodiment of the invention requires a copolymer for rheological or cosmetic compositions comprises a) a first acrylic ester as monomer A, said monomer A being a branched acrylic ester; b) at least one further acrylic ester as monomer B, said monomer B being a linear acrylic ester; c) a cyclic N-vinyl amide as monomer C; d) at least one compound comprising a radically polymerizable α.β-ethylenically unsaturated double bond and at least one cationic and/or cationogenic moiety said compound being monomer D; e) at least one monoethylenically unsaturated carboxylic acid as monomer E; with the monomer B in its polymerized form having a glass transition temperature of −18° C. or lower and making at most 2/7 of the weight amount of monomer A.

The invention also encompasses an embodiment disclosing a copolymer for rheological or cosmetic compositions comprising a) a first acrylic ester as monomer A, said monomer A being a branched acrylic ester; b) at least one further acrylic ester as monomer B, said monomer B being a linear acrylic ester; c) a cyclic N-vinyl amide as monomer C; d) at least one compound comprising a radically polymerizable α.β-ethylenically unsaturated double bond and at least one cationic and/or cationogenic moiety said compound being monomer D; e) at least one monoethylenically unsaturated carboxylic acid as monomer E; with the monomer B in its polymerized form having a glass transition temperature of −18° C. or lower and making at most 1/7 of the weight amount of monomer A.

A still further designed embodiment of the invention is selected from the group consisting of the previously mentioned six embodiments however with the monomer B respectively making at most 1/8 of the weight amount of monomer A.

The cyclic N-vinyl amide as monomer C makes a substantial part of the inventive copolymer since it considerably increases the solubility of the latter in water and consequently also in highly water-loaded solvents. Preferably said cyclic N-vinyl amide is an N-vinyllactam. In an extended embodiment said cyclic N-vinyl amide also comprises derivatives thereof carrying for instance one or more $C_1$-$C_6$-alkyl substituents, such as methyl, ethyl, n-propyl, isopropyl, n-butyl, sec-butyl, tert-butyl etc.

In a more preferred embodiment said monomer C comprises compounds selected from the group consisting of N-vinyl pyrrolidone, N-vinyl piperidone, N-vinyl caprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam.

In a still further preferred embodiment said monomer C is chosen from the group consisting of N-vinyl pyrrolidone, N-vinyl caprolactam, N-vinyl formamide or mixtures thereof with the proviso of N-vinyl formamide always being combined with at least one of N-vinyl pyrrolidone, N-vinyl caprolactam.

The inventive copolymer also requires an entity making a good contact with ceratinic surfaces in particular with hair, the overall charge of which is negative. This need providing to the inventive copolymer a good conditioning capability is satisfied by at least one compound comprising a radically polymerizable α.β-ethylenically unsaturated double bond and at least one cationic and/or cationogenic moiety said compound being monomer D.

In one embodiment said cationic and/or cationogenic moiety of said monomer D is a nitrogen-containing group. This puts the skilled person in a position to selectively choose if and to which extent he wants to have an electron donor in the inventive copolymer.

In a further developed embodiment said cationic and/or cationogenic moiety is selected from the group consisting of primary, secondary and tertiary amino groups.

In an alternative embodiment, said cationic and/or cationogenic moiety is a quaternary ammonium group. However provided that monomer D comprises such quaternary ammonium group such inventive copolymers can only be applied in a non-detrimental way onto a human or animal body in a liquid or solid cosmetic preparation. Quaternary ammonium group is understood within the scope of this invention to be an entity bearing a central nitrogen atom surrounded by four alkyl moieties wherein said moieties are equal or different and contain each at least one carbon atom.

The cationic and/or cationogenic moiety is preferably a tertiary amino group.

Charged cationic groups are to be produced from the amine nitrogen either by protonation, e.g. with carboxylic acids, such as lactic acid, or mineral acids, such as phosphoric acid, sulfuric acid and hydrochloric acid, or by quaternization, e.g. using alkylating agents such as $C_1$- to $C_4$-alkyl halides or sulfates. Examples of such alkylating agents are ethyl chloride, ethyl bromide, methyl chloride, methyl bromide, dimethyl sulfate and diethyl sulfate.

Suitable monomers D are selected from the group consisting of esters of α.β-ethylenically unsaturated mono- and dicarboxylic acids with $C_2$- to $C_{12}$-aminoalcohols said $C_2$- to $C_{12}$-aminoalcohols being $C_1$- to $C_8$-dialkylated on the amine nitrogen. $C_2$- to $C_{12}$-aminoalcohol means an aminoalcohol having a carbon backbone having from 2 carbon atoms to 12 carbon atoms. The term $C_1$- to $C_8$-dialkylated means that two alkyl entities are connected to the aminenitrogen said alkyl entity having a respective number of carbon atoms ranging from 1 to 8 each.

Suitable α.β-ethylenically unsaturated mono- or dicarboxylic acids of these esters are selected from the group consisting of acrylic acid, methacrylic acid, ethacrylic acid, alpha-chloroacrylic acid, fumaric acid, maleic acid, itaconic acid, citraconic acid, mesaconic acid, glutaconic acid, aconitic acid, crotonic acid, maleic anhydride, monobutyl maleate and mixtures thereof. Preference is given to using acrylic acid, methacrylic acid and mixtures thereof.

In a somewhat preferred embodiment suitable monomers D are selected from the group consisting of esters of acrylic acid with $C_2$- to $C_{12}$-aminoalcohols said $C_2$- to $C_{12}$-aminoalcohols being $C_1$- to $C_8$-dialkylated on the amine nitrogen. In a likewise preferred inventive embodiment suitable monomers D are selected from the group consisting of esters of methacrylic acid with $C_2$- to $C_{12}$-aminoalcohols said $C_2$- to $C_{12}$-aminoalcohols being $C_1$- to $C_8$-dialkylated on the amine nitrogen Preferred monomers D are selected from the group consisting of N,N-dimethylaminomethyl(meth)acrylate, N,N-dimethylaminoethyl(meth)acrylate, N,N-diethylaminoethyl(meth)acrylate, N,N-dimethylaminopropyl(meth)acrylate, N,N-diethylaminopropyl(meth)acrylate, N,N-dimethylaminocyclohexyl(meth)acrylate. Among those preference is given to using N,N-dimethylaminoethyl(meth)acrylate or N,N-dimethylaminopropyl(meth)acrylate or mixtures thereof.

Suitable monomers D are also selected from amides of radically polymerizable α.β-ethylenically unsaturated mono- and dicarboxylic acids with diamines which have a tertiary and a primary or secondary amino group. Acyclic diamines are privileged. Preferably such suitable monomers D are selected from amides of the above-mentioned radically polymerizable α.β-ethylenically unsaturated mono- and dicarboxylic acids with acyclic diamines which have a tertiary and a primary or secondary amino group. "Above-mentioned" means the para. disclosing the group of fourteen radically polymerizable α.β-ethylenically unsaturated mono- and dicarboxylic acids and their respective mixtures. The additional effect of such monomers D is their ability not only to interact with negatively charged surfaces in particular negatively charged ceratinic surfaces like hair but further to be highly compatible with peptide bonds due to the amide moiety. Consequently attractive interaction with proteic i.e. ceratinic surfaces is improved.

In a yet more preferred embodiment of this invention suitable monomers D are selected from amides of acrylic acid and/or methacrylic acid with diamines which have a tertiary and a primary or secondary amino group. Still further preferred within said embodiment are acyclic diamines.

Highly preferred embodiments of monomer D are selected from the group consisting of N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide, N-[4-(dimethylamino)cyclohexyl]methacrylamide.

In a mostly preferred embodiment of the invention monomer D ist N-[3-(dimethylamino)propyl]methacrylamide.

A further mandatory part of the copolymer of the invention is at least one monoethylenically unsaturated carboxylic acid as monomer E. "Monoethylenically unsaturated" means that there is only one unsaturated entity within the molecule such entity being in α-vicinity to the carboxylic group. Due to this type of monomer, the solubility in aqueous solutions of the copolymer of the invention is increased.

Said monomer E is an anionogenic or anionic compound. Within the scope of the present invention, an anionogenic compound is understood as meaning a compound which can be converted into the corresponding anionic form by deprotonation with customary, preferably cosmetically acceptable, organic or inorganic bases. This means that the monoethylenically unsaturated carboxylic acid as monomer E comprises within the scope of this invention both the uncharged as well as the negatively charged form thereof.

The wording "monoethylenically unsaturated carboxylic acid as monomer E" likewise comprises at least one entity selected from the group consisting of olefinically unsaturated, free-radically polymerizable carboxylic acids and organic and inorganic salts thereof.

The monomer E is selected from the group consisting of monocarboxylic acids, dicarboxylic acids, carboxylic anhydrides or half-esters of dicarboxylic acids.

Preferably monomer E is selected from the group consisting of acrylic acid, methacrylic acid, ethacrylic acid, alpha-chloroacrylic acid, crotonic acid, maleic acid, maleic anhydride, itaconic acid, citraconic acid, mesaconic acid, glutaconic acid, aconitic acid, fumaric acid, half-esters of olefinically unsaturated dicarboxylic acids having 4 to 10, preferably 4 to 6, carbon atoms and salts thereof.

More preferably monomer E is at least one compound selected from the group consisting of acrylic acid, methacrylic acid, crotonic acid, itaconic acid, salts thereof and mixtures thereof.

In a mostly preferred embodiment monomer E is methacrylic acid. Said monomer per se conveys several advantages to the inventive copolymer. It is easily available and cost-efficient. Furthermore due to its methacrylic character it provides to the inventive copolymer a certain but still moderate character of rigidity and at the same time helps increasing the copolymer's solubility in aqueous solutions.

It is to be mentioned that to a certain extend monomers B and E are responsible for fine-tuning the mechanical properties of the inventive copolymer and thus of inventive compositions thereof. Monomer E plays the role of rendering it more rigid whereas monomer B serves for conferring to it a more flexible character. Both characteristics are required for said fine-tuning however, such effect should not overrule the requirement of sufficiently interacting with a substrate to which the inventive copolymer or the inventive composition thereof is applied.

Substrate within the scope of this invention means any liquid or solid matter, to which the inventive copolymer or an inventive composition thereof is applied. Such substrate preferably comprises the skin and ceratinic surfaces among which hair is particularly preferred. Such substrate in another embodiment also comprises building material. In yet another embodiment such substrate also comprises seeds, native soil and humus.

In order to still ensure a certain copolymer substrate or composition substrate interaction, the sum of monomer B and monomer E does not exceed 20% by weight of the total copolymer weight, is preferably at most 18% by weight, more preferably at most 13% by weight and most preferably at most 8% by weight, with the proviso that the total copolymer weight is the sum of the weight amounts of monomers A to E and corresponds to 100% by weight. Respecting these quantities would still leave sufficient space for the more proteophilic or peptidophilic in particular more ceratinophilic monomers C and D, which when used in higher concentration promote a somewhat stronger interaction with the ceratinic surfaces or the skin. This also contributes to reduce flaking which indeed is observed and outperforms the copolymers of the prior art. Each weight amount of monomers A to E is considered to be the individual weight of the respective monomer.

In the mostly preferred embodiment of the invention monomer C is N-vinyl pyrrolidone since this monomer once polymerized unifies particular features within the copolymer of the invention. First of all it is not toxic and largely used even in pharmacy. Secondly it conveys to the inventive copolymer a high degree of solubility in aqueous solutions. However, once a composition of said copolymer being dried for instance after application on a headdress said monomer C in polymerized form will exercise its propensity for interacting with peptidic or proteic structures like those of the skin or the ceratine of the hair. Due to its medium-sized lactam ring, interaction of monomer C in copolymerized form is neither too pronounced nor to weak.

In a further embodiment of the invention monomer D is a non-quaternized compound, preferably a non-quaternized acrylamide or a non-quaternized methacrylamide. Strong emphasize is given to this embodiment when the inventive copolymer is used in cosmetic compositions designed for being administered in form of a spray or an aerosol. Such compositions were shown to be inoffensive provided that they are non-quaternized. Quaternized within the scope of this invention means that the uncharged amine nitrogen of monomer D either as is or in copolymerized form is converted into a positively charged entity by means of subjecting it to an alkylating agent as specified supra. Non-quaternized therefore means that the amin nitrogen is not positively charged due to the effect of an alkylating agent but has no charge or is positively charged due to the effect of a proton stemming from an organic or inorganic acid.

Non-quaternized (meth)acrylamides are preferred over non-quaternized (meth)acrylates since the former show a greater affinity to proteic or peptidic structures.

In another embodiment of the invention protection is sought for a copolymer wherein the monomer E has a glass transition temperature Tg of 170° C. or more, preferably 190° C. or more. Even more preferred, said glass transition temperature Tg is 210° C. or more or 220° C. or more. It is likewise favorable to have said monomer E to have a glass transition temperature ranging from 210° C. to 230° C. In fact more the glass transition temperature is elevated, more said monomer has a rigid character. Since at least uncontrolled addition of monomer B to the inventive assembly of monomers makes the copolymer thereof softer and a monomer E having a low glass transition temperature would point in the same direction, it is indicated to have this monomer E to have an increased glass transition temperature.

Copolymers having a high negative overall net charge are well adapted to serve as styling polymers, since they do not considerably interact with the likewise negatively charged ceratinic surfaces of the hair but rather force them in a structure predefined by the copolymer itself. Thus a further embodiment of the invention provides a copolymer having a negative net charge when in its non-neutralized and non-quaternized form. Negative net charge as understood within the scope of this invention means that the inventive copolymer is charged negatively when it is in a condition under which no neutralization thereof by means of protons and no quaternization by means of alkylalting agents was realized prior during or after the copolymerization reaction. A non-neutralized form of the inventive copolymer is a form thereof which was not brought to a pH ranging from 6 to 8 and preferably being 7. A non-neutralized form of monomer E is the form said monomer E adopts without being treated by any acids or bases. Non-quaternized means that amin nitrogen atoms are not positively charged due to the effect of an alkylating agent but have no charge or are positively charged due to the effect of a proton stemming from an organic or inorganic acid as previously mentioned.

A negative net charge is favorable for the inventive copolymer. However, provided said net charge is too large this compromises the copolymer's conditioning ability. In particular, their conditioning effect is quite poor since there is repulsion between the negatively charged ceratinic surface and the copolymer. In order to address this need and at the same time to have a certain styling effect one embodiment of the invention arranges for the negative net charge of the inventive copolymer to be smaller than 5, preferably smaller than 4, more preferably between 1 and 3 and most preferably between 2 and 3.

A copolymer providing good interaction with the skin and/or with ceratinic surfaces like hair to which it is applied or a cosmetic composition thereof is to have a good interaction ability with a peptidic or proteic structure. In the case of ceratinic surfaces this requires positively charged structures and as well structures serving as electron donors and electron acceptors capable of interacting with the peptide bonds of the protein e.g. ceratin. Said same interaction ability is also beneficial for improving the mechanical properties of rheological compositions of the invention, for instance their viscosity, their fluidity or their tendency to refrain from disintegration. Furthermore said interaction ability of such inventive rheological compositions is advantageous for their use as rheology modifier or encapsulating means in construction materials; or as emulsifying- or dosage means in agricultural formulations or plant protection formulations. Said interaction ability was shown to be prominent when in another embodiment of the invention the sum of monomer C and monomer D of the inventive copolymer ranges between 45% by weight and 75% by weight of the total copolymer weight, preferably between 47% by weight and 75% by weight, more preferably between 50% by weight and 70% by weight, even more preferably between 50% by weight and 65% by weight, still more preferably between 52% by weight and 65% by weight and most preferably between 52% by weight and 60% by weight, with the proviso that the total copolymer weight is the sum of the weight amounts of monomers A to E and corresponds to 100% by weight. Monomer C shows a propensity to interact with peptide bonds due to its amide structure whereas monomer D when protonated strongly interacts with negatively charged surfaces. However, care should be taken not to only play on the copolymer's ability to interact with peptidic or proteic structures since good solubility of the inventive copolymers in aqueous solutions and a certain copolymer rigidity essential for a styling effect are also required. All these requirements are met by the embodiment set forth previously.

Monomer D provides a substantial contribution to the copolymer's ability to bind to a ceratinic surface and thus fosters its conditioning performance. Monomer E makes the inventive copolymer more soluble in aqueous solvents, makes it more rigid and due to its negative character improves the styling effect thereof. However, in dry form the inventive copolymer should not be too brittle which would lead to partial flaking. Nevertheless the copolymer is to have a good stiffening effect and an increased flexural strength. Further a solution of the inventive copolymer viz. a cosmetic composition thereof should still have a clear aspect and be highly compatible with propellants. In order to meet all this another embodiment of the invention provides a copolymer wherein monomer D is used in a weighting excess with respect to monomer E, said weighting excess being at least 3.5 times the weight amount of monomer E, preferably 5 times the weight amount of monomer E, more preferably 7 times the weight amount of monomer E, still more preferably 8 times the weight amount of monomer E and most preferably 25/3 times the weight amount of monomer E, with the proviso that the total copolymer weight is the sum of the weight amounts of monomers A to E and corresponds to 100% by weight.

A copolymer for rheological or cosmetic compositions fitting with the needs given above is selected from the group consisting of: 30 to 50% by weight of a first acrylic ester as monomer A, said monomer A being a branched acrylic ester; 3 to 20% by weight of at least one further acrylic ester as monomer B, said monomer B being a linear acrylic ester; 15 to 35% by weight of a cyclic N-vinyl amide as monomer C; 15 to 30% by weight of at least one compound comprising a radically polymerizable α.β-ethylenically unsaturated double bond and at least one cationic and/or cationogenic moiety said compound being monomer D; 0.1 to 10% by weight of at least one monoethylenically unsaturated carboxylic acid as monomer E; with the monomer B in its polymerized form having a glass transition temperature of 24° C. or lower and making at most one third of the weight amount of monomer A and with the proviso that the total copolymer weight is the sum of the weight amounts of monomers A to E and corresponds to 100% by weight.

A further advanced copolymer for rheological or cosmetic compositions fitting with the needs given above is selected from the group consisting of: 30 to 50% by weight of a first acrylic ester as monomer A, said monomer A being a branched acrylic ester; 4 to 15% by weight of at least one further acrylic ester as monomer B, said monomer B being a linear acrylic ester; 15 to 35% by weight of a cyclic N-vinyl amide as monomer C; 15 to 30% by weight of at least one compound comprising a radically polymerizable α.β-ethylenically unsaturated double bond and at least one cationic and/or cationogenic moiety said compound being monomer D; 0.1 to 10% by weight of at least one monoethylenically unsaturated carboxylic acid as monomer E; with the monomer B in its polymerized form having a glass transition temperature of 24° C. or lower and making at most one third of the weight amount of monomer A and with the proviso that the total copolymer weight is the sum of the weight amounts of monomers A to E and corresponds to 100% by weight.

A different copolymer for rheological or cosmetic compositions fitting with the needs given above is selected from the group consisting of: 30 to 50% by weight of a first acrylic ester as monomer A, said monomer A being a branched acrylic ester; 3 to 20% by weight of at least one further acrylic ester as monomer B, said monomer B being a linear acrylic ester; 15 to 35% by weight of a cyclic N-vinyl amide as monomer C; 15 to 30% by weight of N-[3-(Dimethylamino)propyl]methacrylamide said compound being monomer D; 0.1 to 10% by weight of at least one monoethylenically unsaturated carboxylic acid as monomer E; with the monomer B in its polymerized form having a glass transition temperature of 24° C. or lower and making at most one third of the weight amount of monomer A and with the proviso that the total copolymer weight is the sum of the weight amounts of monomers A to E and corresponds to 100% by weight.

Yet another embodiment of the invention fitting with the needs given above provides a copolymer for rheological or cosmetic compositions being selected from the group consisting of: 30 to 50% by weight of a first acrylic ester as monomer A, said monomer A being a branched acrylic ester; 3 to 20% by weight of at least one further acrylic ester as monomer B, said monomer B being a linear acrylic ester; 15 to 35% by weight of a cyclic N-vinyl amide as monomer C; 15 to 30% by weight of at least one compound comprising a radically polymerizable α.β-ethylenically unsaturated double bond and at least one cationic and/or cationogenic moiety said compound being monomer D; 0.1 to 10% by weight of methacrylic acid as monomer E; with the monomer B in its polymerized form having a glass transition temperature of 24° C. or lower and making at most one third of the weight amount of monomer A and with the proviso that the total copolymer weight is the sum of the weight amounts of monomers A to E and corresponds to 100% by weight.

Still a further embodiment of the invention fitting with the needs given above discloses a copolymer for rheological or cosmetic compositions being selected from the group consisting of: 30 to 50% by weight of a first acrylic ester as monomer A, said monomer A being a branched acrylic ester; 5 to 10% by weight of at least one further acrylic ester as monomer B, said monomer B being a linear acrylic ester; 15 to 35% by weight of a cyclic N-vinyl amide as monomer C; 15 to 30% by weight of at least one compound comprising a radically polymerizable α.β-ethylenically unsaturated double bond and at least one cationic and/or cationogenic moiety said compound being monomer D; 0.1 to 10% by weight of at least one monoethylenically unsaturated carboxylic acid as monomer E; with the monomer B in its polymerized form having a glass transition temperature of 24° C. or lower and making at most one third of the weight amount of monomer A with the proviso that the total copolymer weight is the sum of the weight amounts of monomers A to E and corresponds to 100% by weight.

In a highly preferred embodiment the copolymer of the invention consists of 30 to 50% by weight of tert.-butyl acrylate as monomer A; 3 to 20 of at least one further acrylic ester as monomer B, said monomer B being a linear acrylic ester selected from the group consisting of n-ethyl acrylate, n-butyl acrylate, n-lauryl acrylate; 15 to 35% by weight of N-vinyl pyrrolidone as monomer C; 15 to 30% by weight of N-[3-(dimethylamino)propyl]methacrylamide as monomer D; 0.1 to 10% by weight of methacrylic acid as monomer E; with the monomer B in its polymerized form having a glass transition temperature of 24° C. or lower and making at most one third of the weight amount of monomer A and with the proviso that the total copolymer weight is the sum of the weight amounts of monomers A to E and corresponds to 100% by weight.

A further inventive embodiment is selected from the group of the previously disclosed six embodiments however with the monomer B in its polymerized form having a glass transition temperature of 10° C. or lower, preferably of 0° C. or lower, more preferably of −18° C. or lower and even of −50° C. or lower.

Yet another embodiment is selected from the group of the previously disclosed seven embodiments however, with the monomer B respectively making at most 2/7 of the weight amount of monomer A, preferably 1/7 or even 1/8 thereof.

Protection is also sought for a process for preparing a copolymer of the invention. Said copolymer is obtained by polymerization in solution comprising the steps: i. preparing an aqueous solution containing between 2 and 60 w % of a mixture of monomer C, monomer D and monomer E; ii. preparing an aqueous solution containing between 2 and 60 w % of a mixture of monomer A, monomer B and monomer D; iii. supplementing an aliquot of the aqueous solution of step i with an aliquot of the aqueous solution of step ii; iv. adding an aliquot of a solution of an initiator Y; v. heating the mixture obtained from steps i. to iv. to a temperature ranging from 60° C. to 120° C.; vi. adding the remainders of the aqueous solutions of steps i., ii. and iv. under stirring; vii. neutralizing the mixture after cooling; and viii. stripping of the solvent at a temperature ranging from 70 to 120° C.

In a highly preferred embodiment of this process the aqueous solutions of step i. and ii. are aqueous solutions comprising isopropanol as cosolvency. In a mostly preferred embodiment the aqueous solutions of step i. and step ii. as solvents only contain water and isopropanol. By using as solvents within said aqueous solutions only water and isopropanol the skilled person is in the position to properly dissolve all of the monomers of the invention viz. hydrophilic and hydrophobic ones without any problem.

A mixture of monomer C, monomer D and monomer E within the scope of the invention is understood to be any mixture of said monomers regardless of the proportion of each monomer as long as the weight amounts or percentage by weight values of each monomer in the inventive copolymer to be synthesized are respected and yield the total copolymer weight.

In a preferred embodiment the weight amount of monomer D used in the mixture of monomer C, monomer D and monomer E is half of the weight amount of monomer D used in total.

A mixture of monomer A, monomer B and monomer D within the scope of the invention is understood to be any mixture of said monomers regardless of the proportion of each monomer as long as the weight amounts or percentage by weight values of each monomer in the inventive copolymer to be synthesized are respected and yield the total copolymer weight.

In a preferred embodiment the weight amount of monomer D used in the mixture of monomer A, monomer B and monomer D is half of the weight amount of monomer D used in total.

Monomer D has both a hydrophobic and a hydrophilic character. It therefore mixes well with hydrophobic and with hydrophilic compounds. In order to arrange for homogeneous and thorough mixing of monomer D during copolymerization, said monomer is equally spread over the aqueous solution containing the mixture of monomer C, monomer D and monomer E and over the aqueous solution containing the mixture of monomer A, monomer B and monomer D.

The aliquot of the aqueous solution of step i. is considered to be any part of the solution of step i. Likewise the aliquot of the aqueous solution of step ii. is considered to be any part of the solution of step ii. The main topic of using only an aliquot of the aqueous solution of step i. is to manage the polymerization reaction properly and homogeneously. Therefore in a preferred embodiment of the invention the aliquot of the aqueous solution of step i. makes from 1/10 to 1/3 of said aqueous solution, preferably from 1/8 to 1/4 thereof and most preferably from 1/7 to 1/5 thereof. For the same reason in an alternative preferred inventive embodiment the aliquot of the aqueous solution of step ii. makes from 1/20 to 1/4 of said aqueous solution, preferably from 1/16 to 1/8 thereof and most preferably from 1/12 to 1/10 thereof.

A very smooth and homogeneous copolymerization is achieved if an aliquot of the aqueous solution of step I. is supplemented with an aliquot of the aqueous solution of step ii, such that the aliquot of the aqueous solution of step i. makes from 1/10 to 1/3 of said aqueous solution and the aliquot of the aqueous solution of step ii. makes from 1/20 to 1/4 of said aqueous solution. Still better results are obtained if an aliquot of the aqueous solution of step I is supplemented with an aliquot of the aqueous solution of step ii, such that the aliquot of the aqueous solution of step i. makes from 1/8 to 1/4 of said aqueous solution and the aliquot of the aqueous solution of step ii. makes from 1/16 to 1/8 of said aqueous solution. One has highly satisfying copolymerization results if an aliquot of the aqueous solution of step I is supplemented with an aliquot of the aqueous solution of step ii, such that the aliquot of the aqueous solution of step i. makes from 1/7 to 1/5 of said aqueous solution and the aliquot of the aqueous solution of step ii. makes from 1/12 to 1/10 of said aqueous solution.

Copolymerization for the inventive copolymer is started by means of an initiator Y. Said initiator Y is selected from the group consisting of peroxo compounds. In particular it is selected from the group including diacetyl peroxide, dibenzoyl peroxide, succinyl peroxide, di-tert-butyl peroxide, tert-butyl perbenzoate, tert-butyl perpivalate, tert-butyl peroxy-2-ethyl-hexanoate, tert-butyl permaleate, diisopropyl peroxy-dicarbamate, bis(o-toluoyl)peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, tert-amyl hydroperoxide, cumene hydroperoxide, pinane hydroperoxide, 2,5-dimethyl-2,5-di(tert-butylperoxy)hexane.

In another embodiment said initiator Y is selected from the group of aliphatic or cycloaliphatic azo compounds. In particular said initiator Y is selected from 2,2'-azobis(isobutyronitrile), 2,2'-azobis(2-methylbutyronitrile) (Wako V-59®), 2,2'-azobis(2,4-dimethylvaleronitrile-), 1,1'-azobis(1-cyclohexanecarbonitrile), 2,2'-azobis(2-amidinopropane) hydrochloride (Wako V-50@), 2-(carbamoylazo)isobutyronitrile, 4,4'-azobis(4-cyanovaleric acid) and the alkali metal and ammonium salts thereof, e.g. the sodium salt, dimethyl 2,2'-azobisisobutyrate, 2,2'-azobis[2-(2-imidazolin-2-yl)propane] (Wako VA-061®), 2,2'-azobis(2-amidinopropane) and the acid addition salts e.g., the dihydrochlorides, dimethyl 2,2'-azobis(2-methylpropionate) (Wako V-601®), Said initiator Y is also selected from the group consisting of hydrogen peroxide, hydroperoxides in combination with reducing agents, and persalts. In particular it is selected from the group of tert-butyl hydroperoxide, tert-amyl hydroperoxide, cumene hydroperoxide and pinane hydroperoxide, in each case in combination with, for example, a salt of hydroxymethanesulfinic acid, an iron(II) salt or ascorbic acid. Suitable persalts are, in particular, alkali metal peroxodisulfates.

Further detailed embodiments of the afore-mentioned initiator Y comprise ascorbic acid/iron(II) sulfate/sodium peroxodisulfate, tert-butyl hydroperoxide/sodium disulfite, tert-butyl hydroperoxide/sodium hydroxymethanesulfinate, $H_2O_2$/Cu and $H_2O_2$/ascorbic acid.

The initiator Y is added to the aliquots of solution i. and solution ii. in a solubilized form. The solution of the initiator Y comprises any solvent which is able to dissolve said initiator. Preferably the solvent of the solution of the initiator Y is at least one polar aprotic solvent or a mixture thereof. In a further preferred embodiment said solvent of the solution of the initiator Y is at least one alcohol or a mixture thereof and in a highly preferred embodiment said solvent of the solution of the initiator Y is isopropanol.

The amount of initiator Y used, is generally in a range of from about 0.1 to 2% by weight, based on the total copolymer weight.

The aliquot of the solution of the initiator Y being at most ½ of the total amount of the solution of the initiator. In a more preferred embodiment thereof, the aliquot of the solution of the initiator Y ranges from ¼₀ to ⅓ of the total amount of the solution of the initiator, preferably from ¹⁄₂₀ to ⅟₇ thereof, more preferably from ¹⁄₁₆ to ¹⁄₁₀ thereof and most preferably from ¹⁄₁₅,₁₂₅ to ¹⁄₁₂ of the total amount of the solution of the initiator. It was shown that quite rapid and homogeneous copolymerization to be achieved by means of respecting the mostly preferred range for said aliquot of the solution of the initiator Y.

High copolymerization yields in considerable time are realized when heating the mixture obtained from steps i. to iv. to a temperature ranging from 60° C. to 120° C., preferably from 70° C. to 100° C. and most preferably form 75° C. to 90° C.

Once copolymerization got started, which is preferably after step v., the remainders of the aqueous solutions of steps i., ii. and iv. are added under stirring. Stirring should be vigorous in order to overcome the still increasing viscosity of the reaction mixture during course of the copolymerization. The remainder of step i. is understood to be the aqueous solution of step i. deduced for the aliquot of the aqueous solution of step i. disclosed in step iii. The remainder of step ii. is understood to be the aqueous solution of step ii. deduced for the aliquot of the aqueous solution of step ii. disclosed in step iii. The remainder of step iv. is understood to be the solution of the initiator Y deduced for the aliquot of said solution of the initiator Y as disclosed in step iv.

In a preferred embodiment the remainder of the aqueous solution of step i. is added during a time ranging from 20 min to 3 h, preferably ranging from 40 min to 150 min and most preferably ranging from 1 h to 2 h respectively under stirring.

In another preferred embodiment the remainder of the aqueous solution of step ii. is added in a time ranging from 2 h to 7 h, preferably from 3 h to 6 h and mostly preferred in a time ranging from 4 h to 5 h respectively under stirring.

Yet another preferred embodiment requires the remainder of the aqueous solution of step iv. to be added during a time ranging from 3 h to 8 h, preferably ranging from 4 h to 7 h and most preferably ranging from 5 h to 6 h respectively under stirring.

In a further embodiment of this invention the addition of the remainders of the aqueous solutions of steps i., ii. and iv. under stirring is realized at the same point in time. This contributes to a smooth run of copolymerization and yields rather homogeneous copolymers.

A highly preferred way of processing is to simultaneously add the remainders of the aqueous solutions of steps i., ii. and iv. under stirring such that the remainder of the aqueous solution of step i. is added during a time ranging from 1 h to 2 h, the remainder of the aqueous solution of step ii. is added during a time ranging from 4 h to 5 h and the remainder of the aqueous solution of step iv. is added during a time ranging from 5 h to 6 h. In fact, it is advantageous to have a slow time of addition of the remainder of the aqueous solution of initiator Y viz. of step iv. said time exceeding the time required for adding the remainders of the aqueous monomer solutions of steps i. and ii., since than the amount of remaining unpolymerized monomers drops considerably. Further it is of great advantage to choose the time for adding the remainder of the aqueous solution of step i. to be shorter compared to this for the remainder of the aqueous solution of step ii. since the monomers of the latter are not as likely soluble in aqueous environments than the monomers of the former. Consequently more time is required to uniformly mix in particular the monomers A and B of step ii. with the copolymerization mixture.

A more elaborated embodiment requires after step vi. to further let the mixture react for a period of time ranging from 1 h to 4 h and preferably from 2 h to 3 h. This supports completion of the copolymerization reaction.

In a further preferred embodiment the process of the invention requires after step vi. to increase the temperature of the mixture in a range varying from 2 to 15° C. and preferably from 5 to 10° C. This further assists to bring forward the reaction rate of the copolymerization.

Still more preferred is to further let the mixture react after step vi. for a period of time ranging from 1 h to 4 h and preferably from 2 h to 3 h and to increase the temperature of the mixture in a range varying from 2 to 15° C. and preferably from 5 to 10° C. This combination of the previously disclosed two measures brings a cumulative benefit with respect to the yield of the inventive copolymer and the reaction speed.

Still another embodiment of the inventive process requires to administer a regulator R. Said regulator R is to be added after step i. or step ii. or step iii. or step iv. or step v. or step vi. and preferably after step i. or step ii. or step iii. or step iv. of the inventive process. Such regulator R arranges for achieving or fine-tuning a desired K value of the copolymers of the invention. The administration is of particular benefit in the case of emulsion or suspension polymerization, copolymerization methods to be used for particular combinations of monomers A, B, C, D and E.

Said regulator is selected from the group consisting of aldehydes, formic acid, ammonium formate, hydroxylammonium sulfate and hydroxylammonium phosphate, compounds which contain sulfur in organically bonded form, compounds which contain sulfur in the form of SH groups, water-soluble, sulfur-containing polymerization regulators, allyl compounds, benzyl compounds or alkyl halides.

Within the aldehydes said regulator is preferably selected from formaldehyde, acetaldehyde, propionaldehyde, n-butyraldehyde and isobutyraldehyde. Within the compound containing sulfur in organically bond form said regulator is preferably chosen form di-n-butyl sulfide, di-n-octyl sulfide, diphenyl sulfide. For compounds which contain sulfur in the form of SH groups, said regulator is preferably selected from n-butyl mercaptan, n-hexyl mercaptan or n-dodecyl mercaptan. Within the water-soluble, sulfur-containing polymerization regulators, the regulator is preferably at least hydrogen sulfite and/or disulfite. A preferred ally compound is allyl alcohol or allyl bromide. A preferred benzyl compound is benzyl chloride. A preferred alkyl halide is chloroform or tetrachloromethane.

Another topic of the inventive process aims to further reduce the amount of not copolymerized monomers and thus to take the copolymerization reaction to a higher conversion, such as, for instance 99.9%.

This is achieved by supplementing the mixture after step vi. with one or more polymerization initiators Y as indicated supra, but different from those used in step iv. More preferred is supplementing the mixture after step vi. with one or more polymerization initiators Y as indicated supra, but different from those used in step iv. and heating the mixture to the polymerization temperature or to temperatures above the polymerization temperature.

Besides the initiators Y mentioned supra, alternatively the mixture after step vi. is supplemented with at least one of all other customary initiators suitable for free-radical polymerization in aqueous solution selected from the group of peroxides, hydroperoxides, peroxodisulfates, percarbonates, peroxo esters and hydrogen peroxide.

Yet an alternative for further reducing the amount of not copolymerized monomers A to E is by means of an acid. For this embodiment, the mixture obtained after step vi. is admixed with water and an acid. Still further preference is given for admixing the mixture obtained after step vi. with water and acid and further heating it. It is highly preferable to admix the mixture obtained after step vi. with water and an acid and further heating it to temperatures of equal or lower than 100° C. And in a mostly preferred embodiment the mixture obtained after step vi. is admixed with water and an acid and further heated to a temperature ranging from 50° C. to 100° C. This way a quite huge amount of not reacted monomers A to E is readily converted to their polymeric or copolymeric forms.

Said acid is selected from the group consisting of organic acids or mineral acids. Within the organic acids said acid is preferably selected from the group of lactic acid, citric acid, acetic acid, oxalic acid, benzoic acid, nicotinic acid. Within the mineral acids said acid is preferably selected from sulfuric acid, hydrochloric acid or phosphoric acid.

Once the initiator Y or a different initiator or an acid is added the reaction mixture is further reacted for another 5 to 15 hours, preferably for another 8 to 12 hours and mostly preferred for another 9 to 10 hours.

After step vi. and the then following potential further steps disclosed supra, the mixture is neutralized after cooling. Cooling is understood to cool the mixture comprising the inventive copolymer to a temperature below 40° C. and preferably to room temperature. Neutralization within the scope of the invention is meant to bring the inventive copolymer to an overall charge which is close to 0 or even 0. This means that one has to play both on the anionic or anionogenic group of monomer E and also on the cationic or cationogenic group of monomer D. In fact what is to be achieved is to obtain a zwitterionic character of the inventive copolymer wherein monomer E is charged negatively to an extent to which monomer D is protonated or alkylated and thus positively charged. This also includes to completely protonate monomer E provided monomer D at the same time remains uncharged.

Such neutralization is to be realized or to be completed by means of at least one organic acid or of at least one mineral acid or by a mixture thereof. The at least one organic is selected from the organic acids mentioned supra and the at least one mineral acids is selected from the mineral acids mentioned supra "Completing" means accomplishing neutralization which was already started, provided that for the purpose of further reducing the amount of not copolymerized monomers A to E or eliminating them an acid was used.

The amount of said at least one organic acid or of that at least one mineral acid or of that mixture thereof is preferably chosen such that a pH in the range from 6 to 7 is reached. By said measure viz. adjusting the mixture of the inventive copolymer to this pH range one obtains copolymers showing the optimum of styling and conditioning performance. Compositions thereof provide a good flexural strength and at the same time maintain conditioning properties. Further they do not show considerable flaking which impacts on the quantity of the copolymer to be consumed for an inventive composition or the amount of inventive composition to be used in an application.

In a highly preferred embodiment of the invention neutralization is to be realized or to be completed by means of 50 w % of phosphoric acid in ethanol or in isopropanol or in a mixture of both. Most preferably neutralization is to be realized or to be completed by means of 50 w % of phosphoric acid in isopropanol. This highly preferred embodiment yielded in short time copolymers of the invention showing excellent styling and conditioning properties and reduced flaking.

Neutralizing the mixture after cooling is to be expedited by means of at least one organic acid or of at least one mineral acid or by a mixture thereof with stirring for a time ranging from 10 min to 3 h, preferably from 20 min to 2 h and most preferably from 30 min to 1 h.

After step vii. the solvent is stripped off at a temperature ranging from 70 to 140° C., preferably ranging from 70° C. to 120° C. and most preferably at a temperature ranging from 80° C. to 110° C. Said stripping off is preferably realized by means of a steam distillation, more preferably by means of a water vapour distillation. By such steam distillation steam-volatile residual monomers or hydrolysis products thereof, and optionally volatile solvents are effectively removed thus leading to rather clean inventive copolymers. Preferably, a steam distillation is carried out until a head temperature of about 110° C. is reached. The term head temperature specifies the temperature given at the head of a distillation column.

An essential part of the invention is a composition comprising at least water and/or a VOC and the copolymer at least as specified in the claims disclosing said copolymer and/or at least as specified in the given description. It is outstanding for this composition that the amount of the copolymer used ranges from 0.001 to 50% by weight, preferably from 0.005 to 30% by weight, more preferably from 0.01 to 20% by weight, further preferred from 0.05 to 20% by weight, even more preferably from 0.1 to 20% by weight and mostly preferred from 0.1 to 15% by weight with respect to the total weight of the composition, said total weight corresponding to 100%. Due to the special styling and conditioning characteristics of the inventive copolymer as shown supra as well as infra in the tables 1 through 3 as well as in the FIGS. 1 and 2, the inventive compositions require much less of the inventive copolymer for obtaining the same styling or conditioning effect. This is to say that approximately only ¾, preferably only ½ and more preferably only ⅓ of the copolymer given in the comparative examples is required for obtaining comparable styling or conditioning effects. Further this low amount of copolymer in the inventive composition substantially contributes to avoid the unpleasant effects of flaking or formation of clumsy or turbid microstructures as can be gleaned from the tables and the figures further specified in detail below. Such results viz. such high flexural strength values paired with a good microstructure, a small droplet size and a good compatibility with propellant are not to be obtained with copolymers of the prior art which are generally used in cosmetic compositions in concentrations ranging from 0.2 to 20 w % with respect to the total weight of the composition.

A VOC within this invention is understood to be a volatile organic compound having an initial boiling point of at most 250° C. at a standard pressure of 101.3 kPa in accordance with Guideline 2004/42/EC.

The total weight of the composition is defined as to be the weight sum of all components of said composition.

In a more preferred embodiment of the inventive composition the VOC is a VOC 80, meaning that the inventive composition comprises at most 80 w % of a VOC. In a still further preferred embodiment the composition comprises a VOC 55, meaning that the composition comprises at most 55 w % of a VOC. Yet a further preferred inventive composition comprises a VOC 35 meaning that only 35 w % of the composition or less are a VOC. Inventive compositions comprising a VOC 55 and still further compositions comprising a VOC 35 are considered to comprise a highly water-loaded solvent, viz. the VOC 55 and at least 45 w % of water. Despite this elevated concentration of water, the composition still tolerates and finely solubilizes the copolymer of the invention which cannot be readily obtained with the polymers of the prior art.

Less the amount of VOC used in the inventive composition is, more readily this composition is adapted to be used in countries allowing only a very low amount of VOC in e. g. cosmetic compositions. Many states of the U.S.A. permit only the use of VOC 55 or even of VOC 35.

Said VOC is selected from the group of VOC1 comprising dimethoxymethane, acetone, dichloromethane, dioxane, $C_2$-$C_6$ monohydric alcohols, such as ethanol, n-propanol, isopropanol, n-butanol, sec-butanol, tert-butanol, n-hexanol, 2-methoxypropan-1-ol, cyclohexanol, benzyl alcohol and the like further from $C_3$-$C_9$ polyols, such as glycerol, glycols like ethylene glycol, propylene glycol, butylene glycol, pentylene glycol, hexylene glycol, butylene glycol, inositol, sorbitol, mannitol, from the methyl or ethyl ethers of the dihydric alcohols such as diethylene glycol, triethylene glycol, polyethylene glycols with number-average molecular weights up to about 3000, and the like, further from hydrocarbons like n-pentane, isopentane, cyclopentane, n-hexane, cyclohexane, n-heptane, n-octane or from mixtures of two or more these compounds.

In a further preferred embodiment the VOC is selected from the group of VOC1 consisting of solvents like dimethoxymethane, $C_2$-$C_6$-monohydric alcohols, such as ethanol, n-propanol, isopropanol, n-butanol, sec-butanol, tert-butanol, n-hexanol, 2-methoxypropan-1-ol, $C_3$-$C_9$ polyols, such as glycerol, glycols like ethylene glycol, propylene glycol, butylene glycol, pentylene glycol, hexylene glycol, butylene glycol, inositol, sorbitol, mannitol, hydrocarbons like n-pentane, n-hexane, cyclohexane, n-heptane, n-octane or from mixtures of two or more of these compounds.

Yet highly preferred is to select the VOC from the group of VOC1 consisting of dimethoxymethane, ethanol, n-propanol, isopropanol, n-butanol, sec-butanol, tert-butanol, inositol, sorbitol and mannitol or mixtures of two or more of these. Such compounds were shown to be highly customer compatible and did show no or almost no allergenic reaction on the surface (ceratinic surface, skin) to which it is applied.

In another embodiment said VOC is selected from the group of VOC2 comprising propellants also named propellant gases or easily vaporizable propellant liquids such as n-propane, isopropane, n-butane, isobutane, 2-methylbutane, 2.2-dimethylbutane, n-pentane, iso-pentanes, dimethyl ether, difluoroethane, fluorotrichloromethane, dichlorodifluoromethane, dichlorotetrafluoroethane, HFC-152 A (1,1-difluoroethane), HFC-134a (1,1,2,2-tetrafluoroethane), hexafluoroethane, specified chlorinated hydrocarbons in small amounts of up to 20% based on the propellant mixture, compressed gases, such as nitrogen, nitrous oxides like e.g. $N_2O$, CO compressed air or carbon dioxide or from mixtures of the group of said propellants.

More preferably said VOC is selected from the group of VOC2 comprising n-propane, isopropane, n-butane, isobutene, n-pentane, dimethylether, compressed air, carbon dioxide or mixtures thereof. Said VOC2 are highly compatible with the skin and ceratinic surfaces and were shown to be environmentally friendly.

In a highly preferred embodiment said VOC is selected from the group being a combination of at least one representative of the VOC1 and at least one representative of the VOC2. Still further preferred is to select said VOC from the group being a combination of one representative of the VOC1 and one representative of the VOC2. Opting for said embodiment of VOC is highly recommended for compositions used in vaporizable means e.g. vaporizable cosmetic means.

In yet another embodiment of the inventive composition preferably cosmetic and even more preferably hair cosmetic composition it comprises as VOC only VOC1, but is still suitable for pump spray preparations.

One embodiment of the composition comprises—water and—at least one VOC selected from the group consisting of ethanol, isopropanol dimethoxymethan, aceton, n-propanol, n-butanol, 2-methoxypropan-1-ol, n-pentan, n-hexan, cyclohexan, n-heptan, n-octan, dichlor-methan,—the copolymer of the invention, the amount of the copolymer used ranging from 0.1 to 15% by weight with respect to the total weight of the composition, said total weight corresponding to 100%. Said copolymer of the invention is neutralized and neutralized as defined as given for vii. of claim 13.

Yet another embodiment of the invention provides a composition comprising at least water and/or a VOC and a copolymer with the amount of the copolymer used ranging from 0.1 to 15% by weight with respect to the total weight of the composition, said total weight corresponding to 100% and with the amount of the copolymer used being ¾ or less, preferably being ½ or less and more preferably being ⅓ or less of the copolymer Amphomer®.

In a more improved form thereof, the invention provides a composition comprising at least water and/or a VOC and the inventive copolymer with the amount of the copolymer used ranging from 0.1 to 15% by weight with respect to the total weight of the composition, said total weight corresponding to 100% and with the amount of the copolymer used being ¾ or less, preferably being ½ or less and more preferably being ⅓ or less of the copolymer Amphomer®.

Still in a further embodiment the composition according to the invention is an aqueous one comprising at least 10% by weight, preferably at least 20 w % more preferably at least 30 w % and particularly preferred between 50 and 80 w % of water, a VOC, at least one cosmetically acceptable carrier B) which is chosen from the group of i) oils, fats, waxes, ii) esters of $C_6$-$C_{30}$-monocarboxylic acids with mono-, di-, trihydric alcohols which are different from ii), saturated acyclic and cyclic hydrocarbons, fatty acids, fatty alcohols, and a copolymer with the amount of the copolymer used ranging from 0.1 to 15% by weight with respect to the total weight of the composition, said total weight corresponding to 100%. Said embodiment comprises a huge amount of water and thus provides a composition which is also accepted in certain U.S. states having a very strict legal act with respect to VOC concentrations.

In a highly preferred embodiment of the invention the composition is an aqueous one comprising at least 10 w %, preferably at least 20 w %, more preferably at least 30 w % and particularly preferred between 50 and 80 w % of water, a VOC, at least one cosmetically acceptable carrier B) which is chosen from the group of i) oils, fats, waxes, ii) esters of $C_6$-$C_{30}$-monocarboxylic acids with mono-, di-, trihydric alcohols which are different from ii), saturated acyclic and cyclic hydrocarbons, fatty acids, fatty alcohols, and a copolymer with the amount of the copolymer used ranging from 0.1 to 15% by weight with respect to the total weight of the composition, said total weight corresponding to 100% and with the amount of the copolymer used being ¾ or less, preferably being ½ or less and more preferably being ⅓ or less of the copolymer Amphomer®.

Mostly preferred the copolymer used in the previous four embodiments is the copolymer of the invention. If the copolymer used is the inventive copolymer, its quantity is reduced with respect to Amphomer®. Consequently less of VOC is required to dissolve this reduced amount. This results in using a larger amount of water and makes the composition still more compatible with environmental issues.

The cosmetically acceptable carrier B) in one embodiment is to be selected from the group of oils, fats and waxes. Said oils, fats and waxes comprise the entities disclosed in Karl-Heinz Schrader, Grundlagen and Rezepturen der Kosmetika, [Fundamentals and formulations of cosmetics], 2nd Edition, Verlag Huthig, Heidelberg, pp. 319-355, said entities being hereby explicitly incorporated by reference.

In particular, said oils are selected from the group consisting of mineral oils; paraffin oils; vaseline; linear saturated hydrocarbons, preferably having more than 8 carbon atoms, such as tetradecane, hexadecane, octadecane and polydecene; branched hydrocarbons like hydrogenated polyisobutene, squalane and squalene, cyclic hydrocarbons, such as decahydronaphthalene cycloparaffin, animal and vegetable oils, synthetic or semisynthetic oils, silicone oils.

Suitable silicone oils are linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1000 to 150 000 g/mol. Preferred cyclic siloxanes have 4- to 8-membered rings. Suitable cyclic siloxanes are commercially available, for example, under the name Cyclomethicone®.

Animal and vegetable oils are selected from the group of natural fats and oils, such as rapeseed oil, castor oil, soybean oil, wheat germ oil, peanut oil, macadamia nut oil, olive oil, sunflower oil, sesame oil, jojoba oil, avocado oil, cocoa butter, almond oil, palm oil, coconut oil, grape seed oil, thistle oil, evening primrose oil, persic oil, ricinus oil, cod liver oil, lard, spermaceti, spermaceti oil, sperm oil. Said animal and vegetable oils are also selected from essential oils of lower volatility, which are mostly used as aroma components or perfume oils. In particular said oils are chosen from the group of sage oil, clary sage oil, camomile oil, oil of cloves, melissa oil, mint oil, eucalyptus oil, cinnamon leaf oil, linden blossom oil, juniper berry oil, vetiver oil, olibanum oil, galbanum oil, labolanum oil, rose hip oil bergamot oil, lemon oil, mandarin oil, orange oil and lavandin oil.

Semisynthetic oils are selected from the group of dihydromyrcenol, lilial, lyral, citronellol, phenylethyl alcohol, a-hexylcinnamaldehyde, geraniol, benzyl acetone, cyclamenaldehyde, linalool, boisambrene forte, ambroxan, indole, hedione, sandelice, allyl amyl glycolate, cyclovertal, □-damascone, geranium oil bourbon, cyclohexyl salicylate, vertofix coeur, iso-E-super, Fixolide NP, evernyl, iraldein gamma, phenylacetic acid, geranyl acetate, benzyl acetate, rose oxide, rommilat, irotyl and floramat.

Fats are also understood to be comprised within the cosmetically acceptable carrier B) as mentioned. Said fats comprise the group of lecithins and fatty acid triglycerides, namely the triglycerol esters of saturated and/or unsaturated, branched and/or unbranched alkanecarboxylic acids with a chain length of from 8 to 24, in particular 12 to 18, carbon atoms. One source of fatty acid triglycerides are synthetic, semisynthetic or natural oils comprising the animal and vegetable oils given supra.

Fats do also comprise chemically modified fats, such as, for instance, hydrogenated vegetable oils like hydrogenated castor oil and/or hydrogenated coconut fatty glycerides, triglycerides, such as, hydrogenated soy glyceride, trihydroxystearin, shea butter, uropygial grease.

Fats frequently used are caprylic/capric triglycerides.

Said waxes of said cosmetically acceptable carrier B) are compounds which at 20° C. are solid to fragile, are susceptible to be kneaded and have a rough to compact grained structure. Their appearance is translucent to opaque, but not vitreous. They melt at temperatures above 40° C. without decomposition and just above said temperature, they are liquid and barely viscous. Their consistency and solubility considerably depends on temperature. Said compounds are susceptible to be polished under moderate pressure.

Typical waxes are selected from the group comprising esters of saturated and/or unsaturated, branched and/or unbranched alkanecarboxylic acids with a chain length from 3 to 30 carbon atoms and saturated and/or unsaturated, branched and/or unbranched alcohols with a chain length of from 3 to 30 carbon atoms as well as from the group of esters of aromatic carboxylic acids and saturated and/or unsaturated, branched and/or unbranched alcohols with a chain length of from 3 to 30 carbon atoms. More preference is given to esters of $C_1$-$C_{24}$-monoalcohols with $C_1$-$C_{22}$-monocarboxylic acids like for instance $C_{20}$-$C_{40}$-alkyl stearate, $C_{20}$-$C_{40}$-alkyl hydroxystearoylstearate.

In a preferred embodiment the wax is selected from the group of isononyl isononanoate, isotridecyl isononanoate, n-hexyl laurate, 2-ethylhexyl laurate, n-propyl myristate, isopropyl myristate, n-propyl palmitate, 2 ethylhexyl palmitate, isopropyl palmitate, hexacosanyl palmitate, 2-octyldodecyl palmitate, octacosanyl palmitate, cetyl palmitate, triacontanyl palmitate, dotriacontanyl palmitate, tetratriacontanyl palmitate, n-butyl stearate, isopropyl stearate, isopropyl isostearate, isooctyl stearate, isononyl stearate, 2-hexyldecyl stearate, 2-ethylhexyl isostearate, hexacosanyl stearate, octacosanyl stearate, triacontanyl stearate, dotriacontanyl stearate, tetratriacontanyl stearate, isopropyl oleate, n-decyl oleate, oleyl oleate, oleyl erucate, erucyl oleate, erucyl erucate, dicaprylyl carbonate (Cetiol CC) dibutyl adipate, 2-ethylhexyl cocoate, cocoglycerides (Myritol 331), glycol esters, such as butylene glycol dicaprylate/dicaprate, dicaprylyl ether, propylene glycol monolaurate, polyethylene glycol monolaurate, glycol montanate, octyldodecanol, isoeicosane, $C_{10}$-$C_{15}$-alkylbenzoate, benzyl benzoate, $C_1$-$C_{10}$-salicylates, e.g. octyl salicylate, $C_{10}$-$C_{15}$-alkyl lactates or from mixtures thereof.

In a further preferred embodiment the wax is selected from the group of mixtures of $C_{12}$-$C_{15}$-alkyl benzoate and 2-ethylhexyl isostearate, mixtures of $C_{12}$-$C_{15}$-alkyl benzoate, 2-ethylhexyl isostearate and isotridecyl isononanoate, mixtures of $C_{12}$-$C_{15}$-alkyl benzoate and isotridecyl isononanoate, mixtures of $C_{12}$-$C_{15}$-alkyl benzoate, 2-ethylhexyl isostearate and isotridecyl isononanoate, mixtures of octyldodecanol, dicaprylyl ether, dicaprylyl carbonate, cocoglycerides, mixtures of $C_{12}$-$C_{15}$-alkyl benzoate and butylene glycol dicaprylate/dicaprate.

Preferred waxes from the group of vegetable waxes, animal waxes, mineral waxes and petrochemical waxes used within the cosmetically acceptable carrier B are beeswax, berry wax, carnauba wax, candelilla wax, ceresine, cork wax, esparto grass wax, guaruma wax, japan wax, jojoba wax, lanolin (wool wax), microwaxes, montan wax, ouricury wax, ozokerite (earth wax), paraffin waxes, ricegerm oil wax, shellac wax, spermaceti, sugarcane wax and mixtures of the abovementioned compounds.

The wax of the cosmetically acceptable carrier B) is also selected from chemically modified waxes and synthetic waxes, such as Syncrowax®HRC (glyceryl tribehenate), Syncrowax®AW 1 C ($C_{18}$-$C_{36}$-fatty acid) and montan ester waxes, sasol waxes, hydrogenated jojoba waxes, synthetic or modified beeswaxes (e.g. dimethicone copolyol beeswax and/or $C_{30}$-$C_{50}$-alkyl beeswax), cetyl ricinoleates, such as, e.g., Tegosoft®CR, polyalkylene waxes, polyethylene glycol waxes.

The cosmetically acceptable carrier B) also comprises at least one fatty acid, which is selected from the group of myristic acid, stearic acid, palmitic acid, oleic acid, linoleic acid, linolenic acid as well as from saturated, unsaturated and substituted modifications thereof.

In another embodiment the carrier B) is at least one fatty alcohol selected from the group of lauryl alcohol, myristyl alcohol, cetyl alcohol, stearyl alcohol, oleyl alcohol, cetyl alcohol, 2-butyloctanol (available commercially, for example, as Isofol®2 (Condea)), 2-hexyldecanol (available commercially, for example, as Isofol®6 (Condea)).

A further substantial part of the invention deals with the use of the inventive copolymer or the inventive composition in hair styling- and/or hair conditioning means; in body care products; as rheology modifier or encapsulating means in construction materials; as emulsifying- or dosage means in agricultural formulations or plant protection formulations.

Hair styling- and/or hair conditioning means within the scope of this disclosure any means adapted to shape or to fashion the hair do. It comprises hair sprays, gels for hair styling and/or hair conditioning comprising liquid gels, foam gels as well as vaporizable gels, foams to be applied to the dry or the wet hair, creams to treat the hair or the skin thereunder, emulsions or suspensions adapted to be kneaded into the hair do and/or the skin of the skull, also lotions for the same purpose, lattices of different viscosities as well as pastes. A use of the inventive copolymer or the inventive composition in such hair styling or hair conditioning means is understood to supplement such respective means either with the copolymer of the invention or with the inventive composition or to prepare such means containing the copolymer of the invention or the composition and to apply said thus obtained means to a hair style.

Body care products comprise any kind of liquid, solid, gaseous or sprayable entity given supra but determined to be used in body care. Their overall composition with respect to cosmetically acceptable carriers B) is adapted for the appropriate use on the body. Examples besides the embodiments given supra are sun screen gels and lotions, shower gels and refreshing gels.

Using the inventive copolymer or a respective composition thereof as rheology modifier means to mix a carrier with said copolymer or with said composition in order to render it more rigid or more flexible depending on whether a macroscopic or a microscopic consideration is made. This is particularly useful for construction materials like concrete, mortar, plaster, construction foams, adhesives, bitumen and glue. Such copolymers or compositions are also adapted for encapsulating construction materials such that they maintain their state of matter even with temperature changes and only after a sudden and considerable change they adopt another state.

The inventive copolymers are also suitable for using them as dosage means in an agricultural formulation. This means that due to their structure they embed seeds, fertilizers or nutrients and allow only a slow release from the cage-like or capsule-like structure formed from the inventive copolymer or copolymer film. In this same regard they are to be employed as emulsifying means, which are required if the above-mentioned fertilizers, seeds or nutrients are to be homogeneously dispersed in a liquid carrier of different polarity. Using the inventive copolymers and the respective compositions in a plant protection formulation is to be understood to provide seeds or whole plants with a protective layer or shield made of the copolymer or the composition of the invention. In another embodiment the inventive copolymer or the respective composition is understood to be a cover or casing arranging for pesticides to be released over a predefined time.

Further features, details and advantages of the invention result from the claims' wording as well as from the following description of embodiments and drawings.

PREPARATION OF THE COPOLYMER

Figure 1:
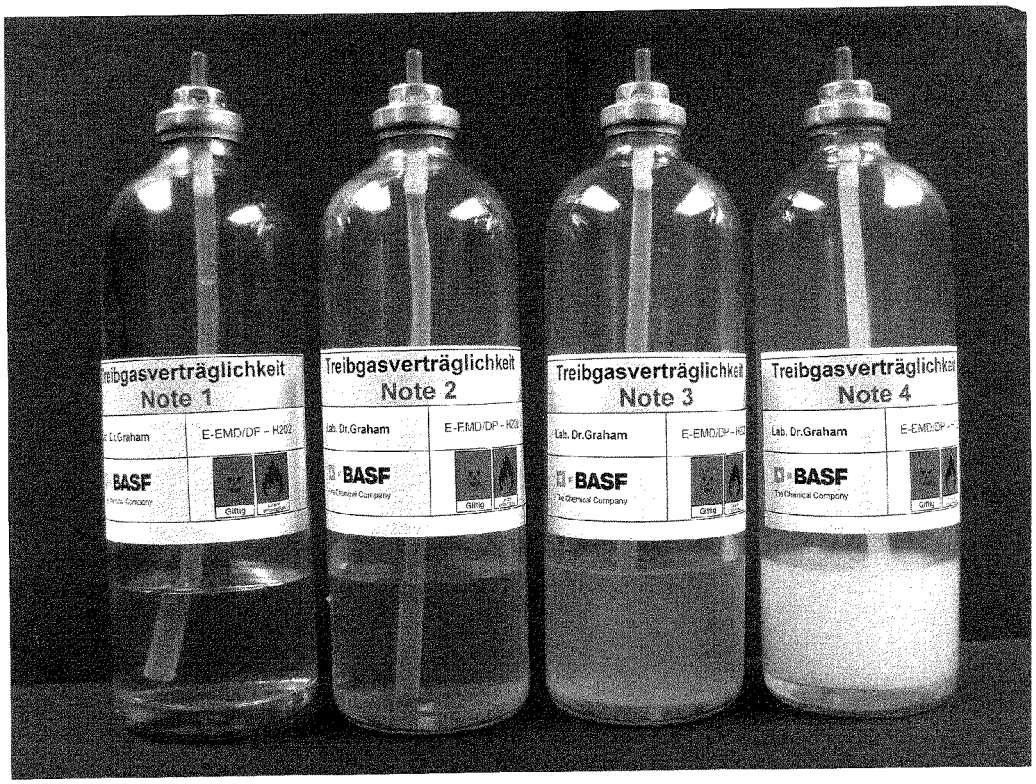
FIG. 1 shows the visual aspect of propellant supplemented polymer solution reference samples.

The preparation of a typical inventive copolymer makes reference to example 1 in table 1 infra and is realized by means of solution polymerization in an isopropanol/water mixture.

Feed 1:
640 g of 1-Vinyl-2-pyrrolidon
296 g of N-[3-(Dimethylamino)propyl]acrylamide
71 g of Methacrylic Acid
Feed 2:
948 g of tert.-Butylacrylate
296 g of N-[3-(Dimethylamino)propyl]acrylamide
118.5 g n-Butyl acrylate
Feed 3
2.5 g of 2,2'-Azobis(2-methylbutyronitril) in 300 g of ethanol Feed 4

7.5 g of 2,5-Bis(tert.-butylperoxi-2,5-dimethylhexane) with the trade name Trigonox® 101 of Akzo Nobel in 500 g of ethanol Feed 5

104 g of phosphoric acid (50% w/v in isopropanol)

⅕ viz. 201.4 g of feed 1, ¹⁄₁₃ viz. 104.8 g of feed 2 and ¹⁄₁₅,₁₂₅ viz. 20 g of feed 3 and 300 g of a mixture of isopropanol/water having a ratio of 1:1 v/v were placed in a stirring means equipped with reflux condenser and three distinct inlets for feeds 1 through 3 and said mixture was heated up to 75° C. while stirring. Once copolymerization had started, which was observed by the initial increase of the mixture's viscosity, the remainder of feed 1 was added in between 1 h, the remainder of feed 2 was added within 4 h and the remainder of feed 3 was added within 5 h while increasing the inner temperature of the means up to 80° C. Once feeding terminated copolymerization was continued for another two hours at said temperature.

Feed 4 was then added within 2 h and further copolymerization was realized for another 10 h at 130° C. under inherent pressure, in order to diminish the amount of residual monomers. (In an alternative the remainder of monomers is to be reduced by means of supplementing water and phosphoric acid to the mixture and subsequent heating thereof of up to 100° C., with phosphoric acid being added in such amount that a pH ranging from 4.5 to 5.5 is reached, which corresponds to a degree of neutralization of the N-[3-(Dimethylamino)propyl]acrylamide used ranging from 80 to 120 mol %.) Subsequently a steam distillation is realized.

Once the mixture being cooled down it is neutralized by means of feed 5, which is supplemented in between 30 min with continuous stirring.

The copolymer solution thus obtained is susceptible to be supplemented with further water after which isopropanol is to be removed by distillation in order to yield aqueous (micro)dispersions of the inventive copolymer. Powdery embodiments of the inventive copolymer are obtained by means of spray drying or lyophilization.

Further inventive copolymers are to be obtained by the previously given protocol however respecting the required monomers and quantities inter alia indicated in table 1 infra.

Preparation of a Cosmetic Composition of the Invention

A typical inventive cosmetic composition among other such inventive compositions is prepared as follows: The inventive copolymer is dissolved in the required amount of ethanol to give a 5% by weight solution. Thus also a copolymer solution per se is understood to be an inventive composition The aspect of the copolymer solution is to be monitored by a testing panel of five persons. They evaluate the appearance of the rheological or cosmetic composition further its homogeneity and its colour.

The appearance is determined to be clear (1), almost clear (2), clouded (3) or turbid (4).

The homogeneity of the copolymer solution dried on a glass plate as a copolymer film was determined by a testing panel of five persons and evaluated on a scale from 1 to 4 with:

1=very homogenous film, no inclusions
2=homogenous film with very small irregularities
3=homogeneous film showing already some aberrations
4=irregular structure almost no continuous film Compatibility with propellant is assessed by applying a propellant gas to a solution containing the inventive polymer and comparing it with reference samples as shown in FIG. 1. The solution chosen and the concentration of the inventive polymer therein are identical for the inventive copolymer and the reference samples. Likewise the pressure and type of propellant gas employed are identical. Compatibility is determined as follows:

1=excellent compatibility, solution remains limpid and mobile, cf. left bottle of FIG. 1
2=good compatibility, solution is slightly turbid and mobile cf. second bottle from the left of FIG. 1
3=moderate compatibility, solution is turbid, less mobile as in third bottle from the left of FIG. 1
4=poor compatibility, solution is opaque and has a higher viscosity, cf. right bottle of FIG. 1

Determination of the Stiffening Effect of a Copolymer Solution Treated Hair Strand:

1 g of copolymer solution was applied onto a hair strand having a length of approximately 23 cm and spread in the hair strand's direction with the fingers. Said strand was dried over night at room temperature and analyzed by a test panel of five persons the next day. The results obtained are ranged as follows:

1=very good stiffening effect
2=good stiffening effect
3=still good stiffening effect
4=poor stiffening effect Washability was determined as follows: A hair strand treated with a respective copolymer solution of the invention is washed in a 37° C. solution containing Texapon-NSO (CAS 68891-38-3) by soaking it and squeezing it for 15 sec. This is repeated five times. Thereafter the strand is rinsed for 15 sec. with tab water. This soaking, squeezing and rinsing is once repeated. The strand is then squeezed onto filter paper and dried over night. The washability will be determined the next day. Parameters evaluated by the test panel of five persons are the strands ability to be combed, its tendency to stick, its sensation when grasped and the quantity of composition residues The results obtained are:

| | |
|---|---|
| very good (1) | all parameters are excellent |
| good (2) | at least three of the four parameters are excellent |
| still good (3) | two of the parameters are excellent |
| not good (4) | does not meet the previously mentioned criteria |

Determination of the Flexural Strength Bt of a Hair Strand Treated with a Hair Styling Composition of the Invention:

A dried hair strand having a length of 24 cm was weighed. 3 g thereof were immersed in the copolymer solution previously prepared, removed thereof and excess solution was stripped. Immersing, removing and stripping was realized three times in order to achieve a homogeneous repartion of the solution in the hair strand.

The last stripping of excess solution was done with thumb and forefinger. Further removal of the solution was realized by pressing the hair strand between filter paper such that the hair strand's weight increases by 1 to 1.4 g (with regard to the initial weight of the hair stand). The strand thus obtained was arranged in order to have a round cross-section and was stored at 20° C. and 65% of relative humidity over night in a climatic chamber.

Analysis of the strand prepared was realized in the climatic chamber having the climatic conditions mentioned before by means of a pull and compression analyzer (Easytest 86 8002, Fa. Frank). The hair strand was placed in a symmetrical way on two cylindrical rolls of the sample holder, said rolls having a diameter of 4 mm and being separated from each other by a distance of 9 cm). By means of a rounded stamp approached from the upper side of the strand and in the exact middle thereof the strand was bent by 40 mm which leads to fracture the copolymer film obtained on the strand. The force required therefore is determined in cN by means of a load cell.

Microstructure, Flaking: A hair strand is subjected to electron microscopy (light microscopy). The results obtained are grouped as follows:

clumpy/clumsy: formations of bulky copolymer aggregates on the hair flaky: occurrence of copolymer flakes on the hair surface or hair pellicle regular: finely dispersed copolymer film on the hair capable of maintaining the surface microstructure of the treated hair.

TABLE 1

| Ex. | MMA | OAM | tBAEMA | AS | HPMA | |
|---|---|---|---|---|---|---|
| V1 | 35 | 40 | 6 | 15 | 5 | |
| | TBA | VP | DMAPAM | MAS | Fifth Monomer | Siloxane |
| V2 | 30 | 27 | 17* | 5 | 19% nBA | 2 |
| | TBA | VP | DMAPMAM | MAS | Fifth Monomer | Siloxane |
| V3 | 50 | 28 | 15 | 6 | — | 1 |
| V4 | 45 | 27 | 25 | 3 | — | — |
| 1 | 40 | 27 | 25 | 3 | 5% nBA | |
| 2 | 35 | 27 | 25 | 3 | 10% nBA | |
| 3 | 40 | 27 | 25 | 3 | 5% LA | |
| 4 | 40 | 27 | 25 | 3 | 5% EA | |

MMA Methylmethacrylate
OAM: Octylacrylamide
tBAEMA 2-(tert.-Butylamino)ethyl methacrylate
AS Acrylic Acid
HPMA Hydroxypropylmethacrylate
TBA tert.-Butylacrylate
VP 1-Vinyl-2-pyrrolidon
DMAPAM N-[3-(Dimethylamino)propyl]acrylamide
DMAPMAM N-[3-(Dimethylamino)propyl]methacrylamide
MAS Methacrylic Acid
nBA n-Butyl acrylate
LA Lauryl acrylate
EA Ethyl acrylate
Siloxane ethoxylated polysiloxane (Belsil ® DMC 6031 of Wacker Chemie GmbH)
INCI Name: PEG/PPG-25/25 Dimethicone viz. the alkoxylated derivative of Dimethicone (q.v.) containing an average of 25 moles of ethylene oxide and 25 moles of propylene oxide

TABLE 2

| Ex. | Aspect Co-polymer Solution | Homogeneity Co-polymerfilm on Glass Plate | Compatibilty with Propellant | Stiffening Effect | Washability | Flexural strength [cN] |
|---|---|---|---|---|---|---|
| V1 | 1 | 1 | 1 | 1-2 | 2 | 165 |
| V2 | 1-2 | — | 1-2 | 1-2 | 1 | — |
| V3 | 1 | 1 | 1 | 2 | 3 | 185 |
| V4 | 4 | 3 | 3-4 | — | — | nd |
| 1 | 1 | 2 | 1 | 1-2 | 2 | 255 |
| 2 | 1 | 1 | 1 | 1-2 | 3 | 210 |
| 3 | 1 | 1 | 1 | 1 | 2 | 527 |
| 4 | 1 | 1 | 1 | 1 | 2 | 516 | nd The flexural strength cannot be determined

TABLE 3

| Ex. | Plasticity | Elasticity | Spraying Pattern Particle Size [μm] | Microstructure/Flaking | Copolymer Portion required to obtain a defined flexural strength |
|---|---|---|---|---|---|
| V1 | 0.06 | 0.51 | 89 | clumpy/clumsy | 1 |
| V2 | — | — | — | — | 1 |
| V3 | — | 0.65 | 57 | flaky | 1 |
| V4 | — | — | — | flaky | 1 |
| 1 | 0.91 | 0.65 | 41 | regular | ~½ |
| 2 | 0.9 | 0.65 | 63 | regular | ~¾ |
| 3 | — | 0.89 | 33 | regular | ~⅓ |
| 4 | — | 0.79 | 35 | regular | ~⅓ |

All solvents (water and/or VOC) typically used in an inventive composition of the copolymers of the invention confer to said composition a clear aspect which can be gathered from table 2 column 2. Said results were obtained with an ethanolic solution of the inventive copolymer as previously indicated. One observes that the results are better or at least identical to those of the comparative experiments. However, comparative example V4 is shown to largely under-perform. Similar results were obtained with methanol or with isopropanol.

All copolymers of the invention exhibit a tendency to form very regular films on a glass plate (cf. table 2, column 3). For all except one of the exemplified copolymers very homogeneous films with no inclusions are obtained and one thereof provides a homogenous film with very small irregularities. Thus the requirements of the comparative examples could be easily met and in some cases even be outperformed.

A further very important issue is the inventive compositions' compatibility with respect to propellants. The visual impact of such compatibility is shown in FIG. 1 and one can observe that especially in transparent containers or on dark hair, compositions as shown in the outer right bottle of said FIG. 1 are not acceptable. Column 4 of table 2 shows all exemplified copolymers to perform extraordinary since the respective pressurized solution remains limpid and mobile. This is at least equal to some of the comparative examples but mostly far better. However, comparative example V4 shows a pretty bad result in this regard.

The inventive compositions' ability to stiffen a hair do is good to very good and outperforms comparative example V3 (cf. column 5 of table 2).

The washability is shown to be better or at least similar to this one of the comparative examples V1 to V4. This assures a long lasting styling and conditioning effect even in stormy or rainy weather The flexural strength provides a means for monitoring the rigidity or flexibility of a copolymer film formed on a hair do or a copolymer layer located within a cosmetic composition like for instance a cream. More the value is high more a film or a layer can be bent without causing partial or total fracture thereof. Thus high values are highly preferable since they protect a headdress or a cosmetic composition or a surface subjected therewith from mechanically caused damage. Column 7 in table 2 shows that every exemplified cosmetic composition outperforms the comparative examples.

Regarding plasticity in column 2 of table 3, only values for some examples and comparative examples were recorded or obtained. Despite the incompleteness of these data it can however be observed that results obtained for inventive compositions are more than ten times larger compared to comparative examples.

Likewise the elasticity of the films or surfaces evolving from the inventive cosmetic compositions is mostly approximately 20% or more elevated and at least comparable to the comparative examples.

One prerequisite for forming a homogeneous regular and thin copolymer film on a ceratinic surface like hair or on the skin is to finely spread the respective cosmetic composition onto the destined surface. This can be assured by forming small droplets either within an emulsion or within an atomized spray. However said droplet size depends on the cosmetic composition and in particular on the inventive copolymer incorporated therein. In this regard the inventive compositions forming droplets having a particle size of 33 and 41 outperform the comparative examples and example 2 only shows a slightly larger particle size or droplet size compared to comparative example 3 (cf. column 4 of table 3).

For the invention disclosed herein great emphasize was given to avoid flaking which is easily observed with dark hair. In this same context a clumpy or clumsy aspect of the treated hair, ceratinic surface or skin should also be avoided, since this prevents from conferring to said hair, ceratinic surface or skin a smooth and glossy non-sticky feel and a fine appearance not disturbed by clumpy or clumsy copolymer aggregates. To establish the potential of the inventive compositions in this regard LM-micrographs were recorded (cf. FIG. 2a to e).

Figure 2A:
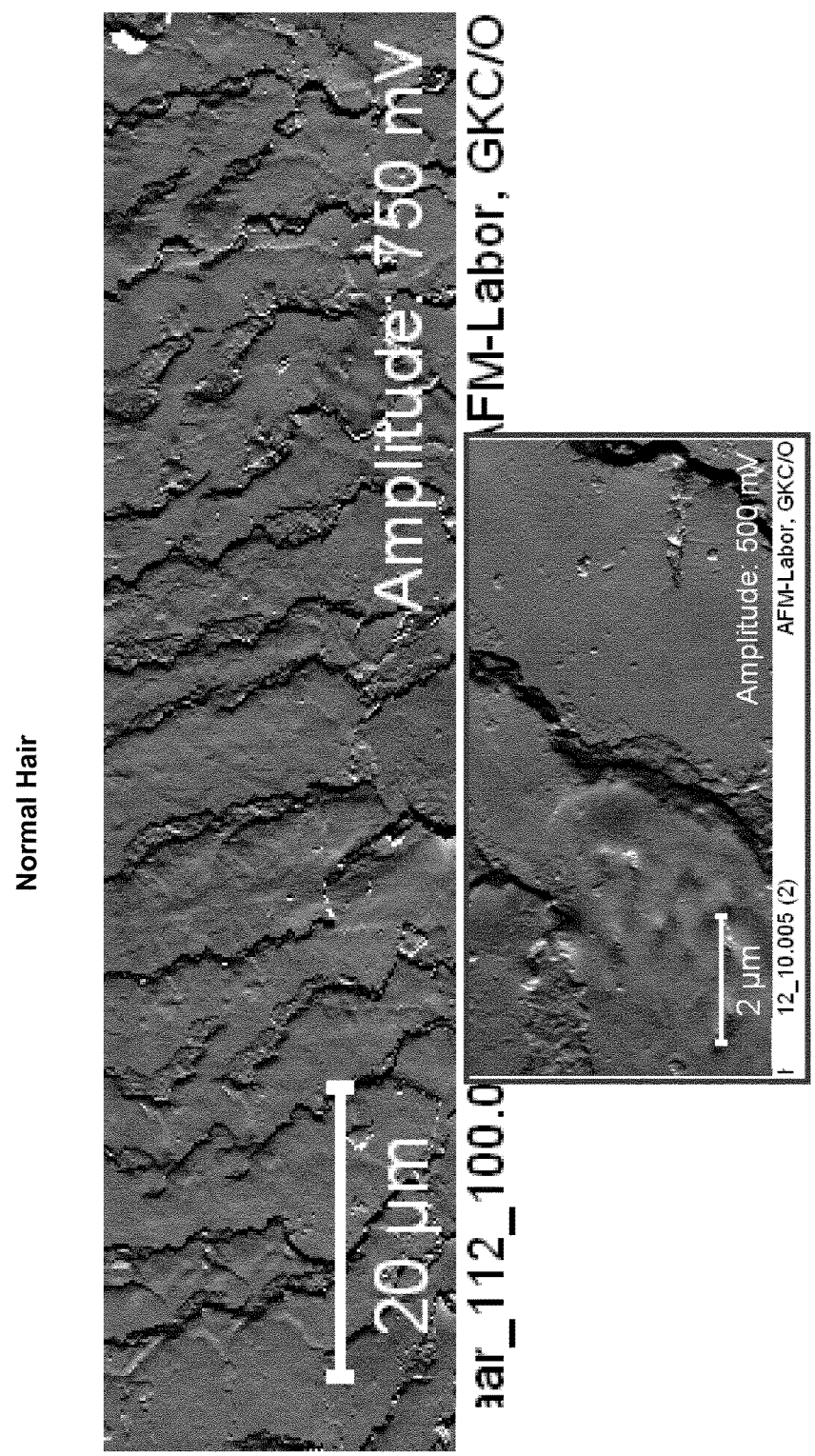
FIG. 2a shows the microscopic surface structure of untreated Caucasian hair.

FIG. 2a depicts untreated Caucasian hair. A normal finely layered slate roof structure of ceratinic blocks can be observed.

Figure 2B:
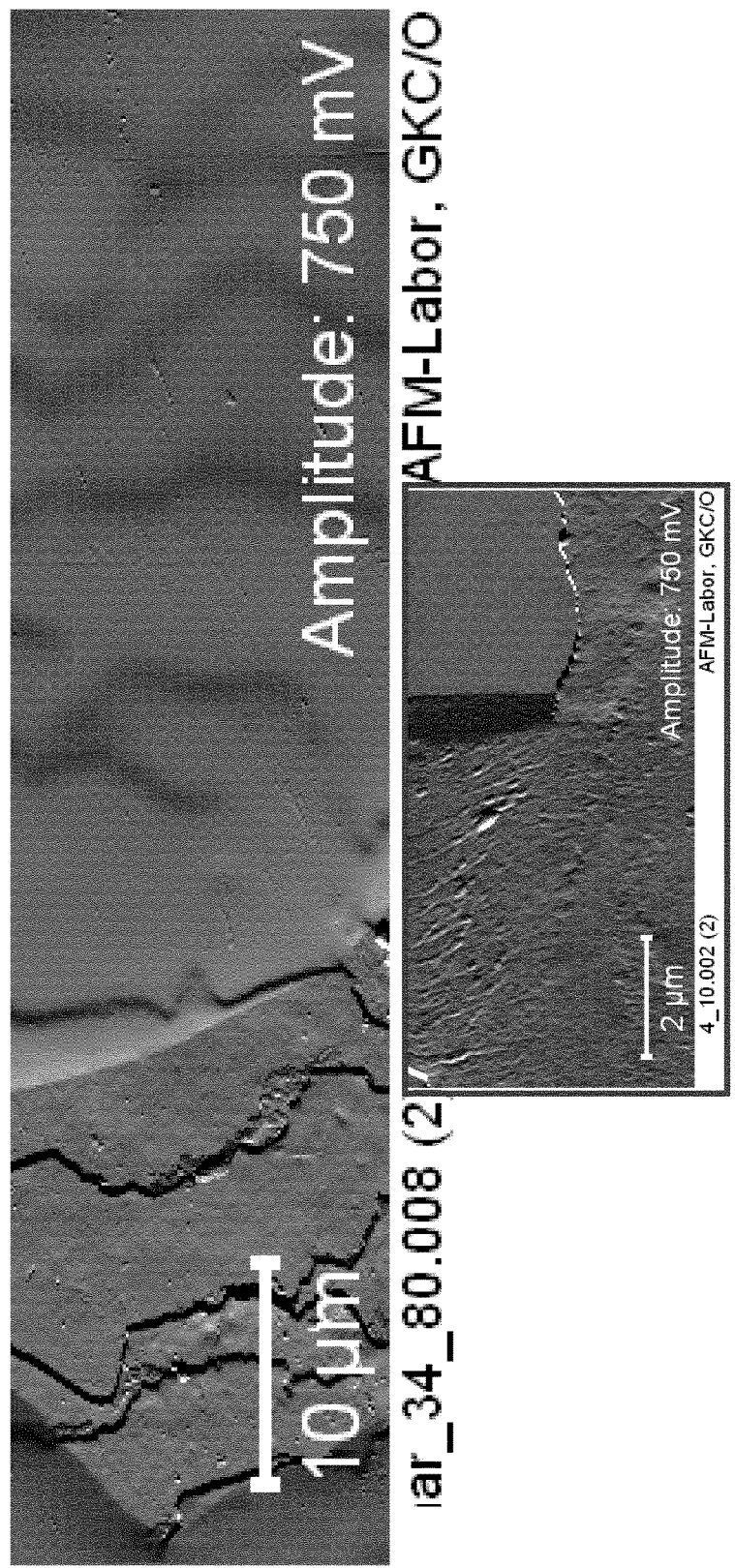
FIG. 2b shows the microscopic surface structure of hair treated with Amphomer®.

In FIG. 2b an ethanolic solution of the commercially available copolymer Amphomer® (CAS-No. 70801-07-9) was applied as cosmetic composition of the prior art to said Caucasian hair. One observes in the right part of said figure a clumsy polymer aggregate completely covering the slate roof structure of the untreated hair. Such heterogeneous polymer repartition yields a sticky sensation and a dim and dull aspect of the hair style. Styling cannot be as efficient as it might be and thus more cosmetic composition and in particular polymer is required in order to obtain the same styling effect. Furthermore, such microscopically huge aggregates are prone to at least partially decompose as a result of mechanical stress, which would result in flaking to at least some extent.

Figure 2C:
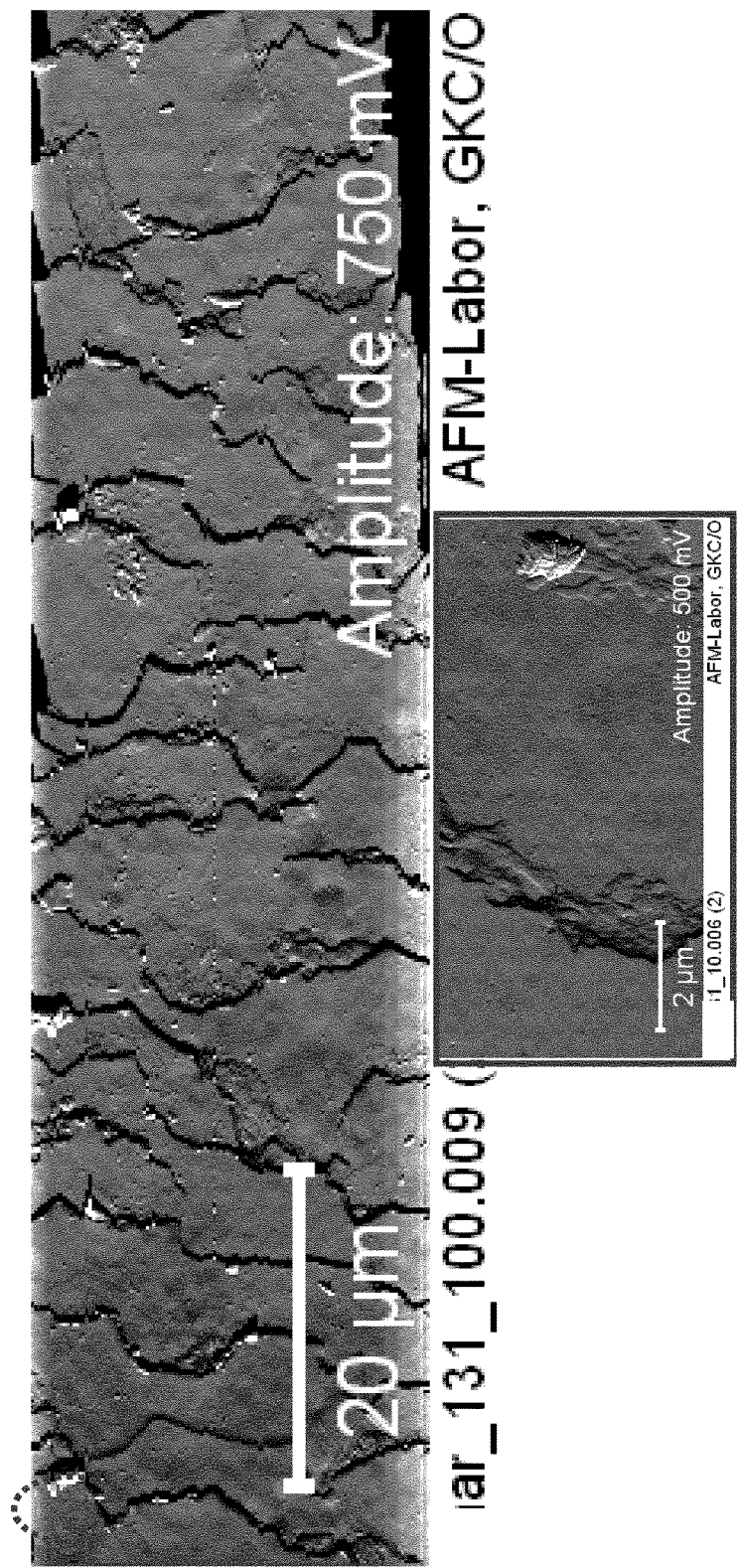
FIG. 2c shows the microscopic surface structure of hair treated with a composition comprising a copolymer as specified in comparative example V3 or V4.

Untreated Caucasian hair is treated in FIG. 2c with a composition comprising a copolymer as specified in comparative example V3 or V4. It is to be noted that compositions comprising such polymer are able to conserve the slate roof structure of untreated hair. However, an increased amount of flakes is observed, which makes the use of such cosmetic composition somewhat unpleasant especially for dark haired people. This is still to be ameliorated.

Figure 2D:
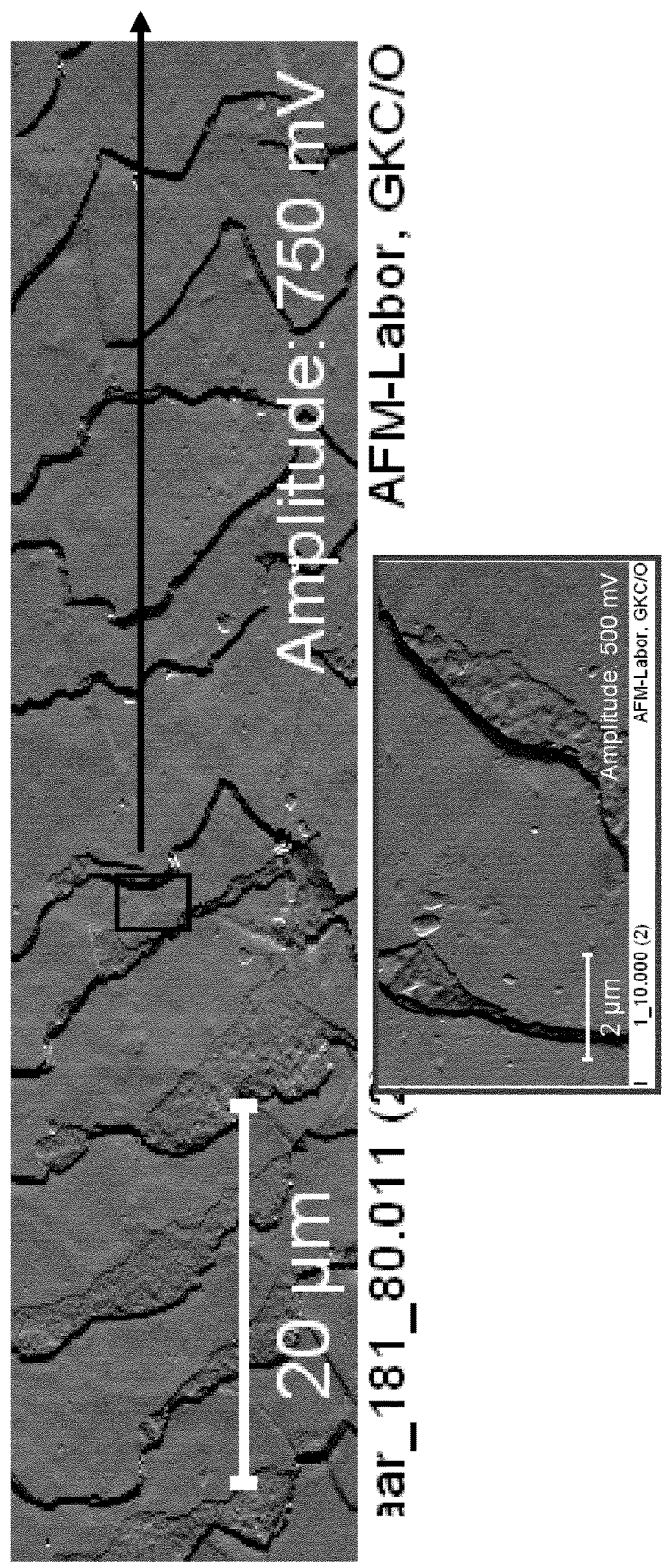
FIG. 2d shows the microscopic surface structure of a hair treated with a composition comprising an inventive copolymer.

The hair strand exposed in FIG. 2d was treated with a cosmetic composition of an inventive copolymer. Similar to FIG. 2c the slate roof structure of untreated hair is properly maintained. However, this is achieved without any detrimental flaking phenomenon. Thus a cosmetic composition comprising the newly developed family of inventive copolymers is also readily applicable for the huge quantity of dark-haired people.

Figure 2E:
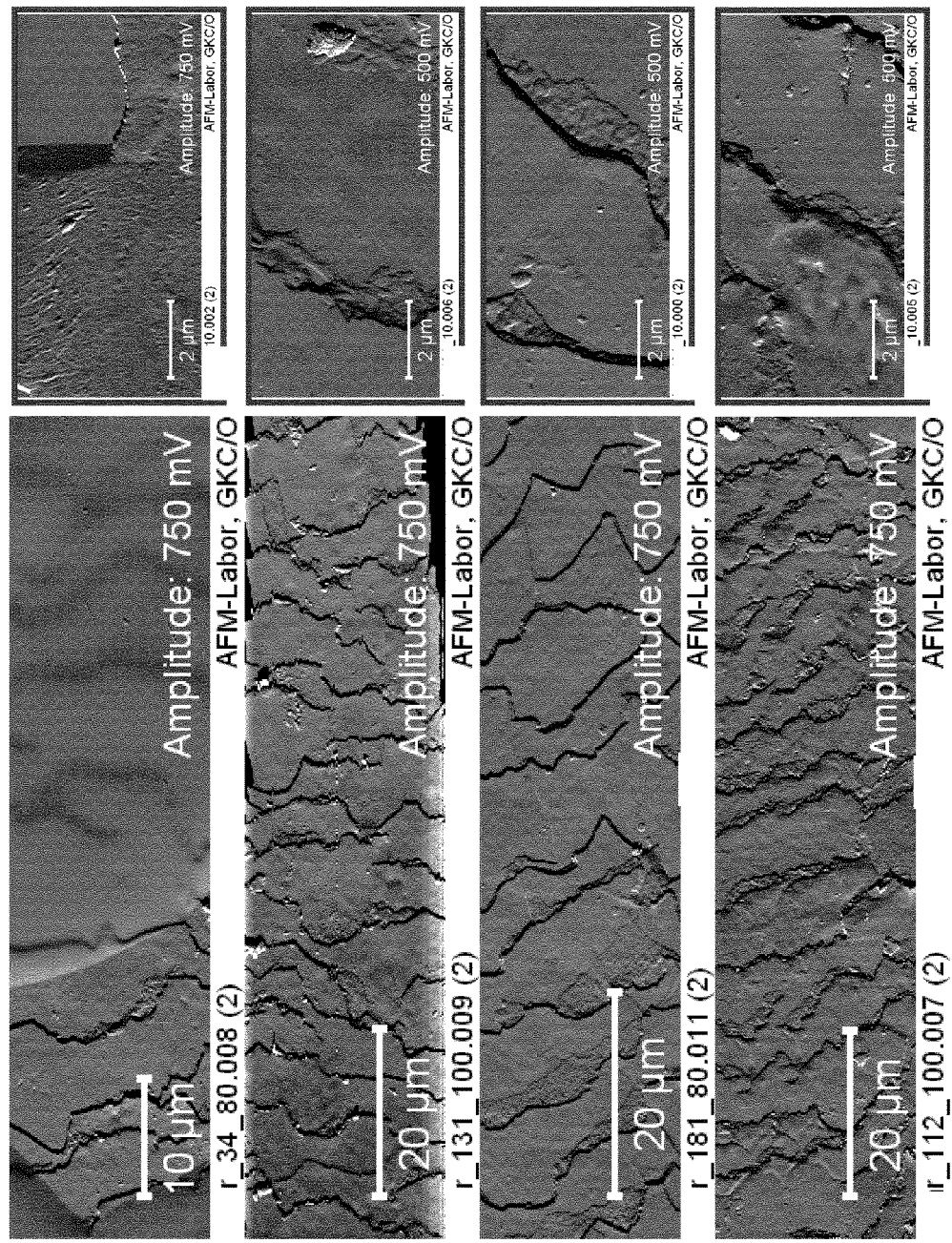
FIG. 2e shows a compilation of FIGS. 2a through 2d.

The aforementioned results can be recapitulated from FIG. 2e making a compilation of FIGS. 2a to 2c. They are also listed in column 5 of table 3.

Another important aspect of the invention was to improve the prior art with respect to costs of the copolymer used for styling purposes. Column 6 in table 3 shows the amount of copolymer to be required for one and the same styling result to be dramatically decreased for the inventive embodiments. At most ¾ of the amount required in the comparative examples and at best only ⅓ thereof is needed when employing inventive embodiments.

One observers that the present invention deals with a copolymer for rheological or cosmetic compositions, a process of making it, a composition thereof and a method of producing said composition. Also within the scope of the invention are selected uses of either the copolymer or the composition thereof. Said copolymer comprises a) a first acrylic ester as monomer A, said monomer A being a branched acrylic ester; b) at least one further acrylic ester as monomer B, said monomer B being a linear acrylic ester; c) a cyclic N-vinyl amide as monomer C; d) at least one compound comprising a radically polymerizable α.β-ethylenically un-saturated double bond and at least one cationic and/or cationogenic moiety said compound being monomer D; e) at least one monoethylenically unsaturated carboxylic acid as monomer E; with the monomer B in its polymerized form having a glass transition temperature of 24° C. or lower and making at most one third of the weight amount of monomer A.

The invention claimed is:

1. A copolymer for rheological or cosmetic compositions comprising:
a) 30 to 50% by weight tert-butyl acrylate as monomer A;
b) 3 to 20% by weight acrylic ester as monomer B, wherein the monomer B has an ester moiety, wherein the ester moiety is COO—$C_1$-$C_{14}$-alkyl;
c) 15 to 35% by weight N-vinyl pyrrolidone as monomer C;
d) 15 to 30% by weight N-[3-(dimethylamino)propyl] methacrylamide being monomer D;
e) 0.1 to 10% by weight methacrylic acid as monomer E; with the monomer B in its homopolymerized form having a glass transition temperature of 24° C. or lower and making at most one third of the weight amount of monomer A, wherein:
a sum of monomer B and monomer E does not exceed 20% by weight of the total copolymer weight,
a sum of monomer C and monomer D ranges between 45% by weight and 75% by weight of the total copolymer weight, and
the monomer D is used in a weighting excess with respect to monomer E, said weighting excess being at least three and one half times the weight amount of monomer E, with the proviso that the total copolymer weight is the sum of the weight amounts of monomers A to E and corresponds to 100% by weight.

2. A composition comprising at least:
water and/or
aVOC
and the copolymer according to claim 1;
wherein
the amount of the copolymer used ranges from 0.001 to 50% by weight, with respect to the total weight of the composition, said total weight corresponding to 100%.

3. The composition according to claim 2 that is effective:
for hair styling and/or hair conditioning,
for body care products,
as rheology modifier in construction materials; or
in agricultural formulations or plant protection formulations.

4. The copolymer according to claim 1 wherein the ester moiety of monomer B is COO—$C_2$-$C_{12}$-alkyl.

5. The copolymer according to claim 1 wherein the ester monomer B is selected from the group consisting of n-butyl acrylate, lauryl acrylate, and ethyl acrylate.

* * * * *